(12) United States Patent
Nies et al.

(10) Patent No.: US 11,596,704 B2
(45) Date of Patent: Mar. 7, 2023

(54) PROCESS MONITORING DEVICE

(71) Applicant: 3M INNOVATIVE PROPERTIES COMPANY, Saint Paul, MN (US)

(72) Inventors: Timothy J. Nies, Stillwater, MN (US); G. Marco Bommarito, Stillwater, MN (US); Christopher J. Claypool, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 867 days.

(21) Appl. No.: 16/466,330

(22) PCT Filed: Dec. 7, 2017

(86) PCT No.: PCT/US2017/065009
§ 371 (c)(1),
(2) Date: Jun. 4, 2019

(87) PCT Pub. No.: WO2018/106860
PCT Pub. Date: Jun. 14, 2018

(65) Prior Publication Data
US 2019/0381204 A1    Dec. 19, 2019

Related U.S. Application Data

(60) Provisional application No. 62/431,562, filed on Dec. 8, 2016.

(51) Int. Cl.
*A61L 2/28*     (2006.01)
*G01N 21/78*    (2006.01)
(Continued)

(52) U.S. Cl.
CPC ............... *A61L 2/28* (2013.01); *G01N 21/78* (2013.01); *C08G 63/183* (2013.01);
(Continued)

(58) Field of Classification Search
CPC ........ A61L 2/28; C08G 63/183; G01N 21/78; G01N 31/226; G01N 2021/7763; G01N 2021/7796
See application file for complete search history.

(56) References Cited

U.S. PATENT DOCUMENTS

| 6,410,338 B1 | 6/2002 | Lippold et al. |
| 6,566,090 B2 | 5/2003 | Witcher |

(Continued)

FOREIGN PATENT DOCUMENTS

| CN | 102781360 A | 11/2012 |
| CN | 103555107   | 2/2014  |

(Continued)

OTHER PUBLICATIONS

International Search Report for PCT International Application No. PCT/US2017/065009, dated Apr. 14, 2018, 5 pages.

(Continued)

*Primary Examiner* — Robert J Eom

(57) ABSTRACT

The present disclosure relates to an article for detecting a disinfectant via visual feedback. The article have a first substrate with a first major surface and opposite ends. The article also comprises a process indicator disposed on at least a portion of the first major surface. The process indicator reacts with at least one liquid disinfectant selected from the group consisting of glutaraldehyde, ortho-phthalaldehyde, hydrogen peroxide, peroxyacetic acid, and combinations thereof. The process indicator can be formed from a synthetic amine-containing polymer derived from polyethylenimine (PEI). The article can have a flow channel that is formed by a portion of the process indicator and that extends between the opposite ends. The disclosure also relates to a kit containing the article as well as a method of using the article in a disinfection process. The article is used to (Continued)

diagnose issues in an automated endoscope reprocessors (AERs).

13 Claims, 6 Drawing Sheets

(51) Int. Cl.
*C08G 63/183* (2006.01)
*G01N 31/22* (2006.01)
*G01N 21/77* (2006.01)

(52) U.S. Cl.
CPC ... *G01N 31/226* (2013.01); *G01N 2021/7763* (2013.01); *G01N 2021/7796* (2013.01)

(56) References Cited

U.S. PATENT DOCUMENTS

| | | | |
|---|---|---|---|
| 7,481,975 B2 | 1/2009 | Read | |
| 7,670,552 B2 | 3/2010 | Read | |
| 8,551,894 B2 | 10/2013 | Seshadri | |
| 2003/0215923 A1* | 11/2003 | Witcher | G01N 31/226 435/71.1 |
| 2007/0154703 A1 | 7/2007 | Waller | |
| 2008/0261296 A1* | 10/2008 | Justi | A61L 2/28 435/287.4 |
| 2011/0064606 A1* | 3/2011 | Foltz | C12Q 1/22 422/119 |
| 2011/0182770 A1* | 7/2011 | Chandrapati | C12Q 1/22 422/292 |
| 2015/0165082 A1 | 6/2015 | Chandrapati | |
| 2015/0203790 A1 | 7/2015 | Strerath | |
| 2015/0232673 A1 | 8/2015 | Jing | |
| 2015/0246350 A1 | 9/2015 | Sun | |
| 2015/0252196 A1 | 9/2015 | Jing | |
| 2016/0096802 A1 | 4/2016 | Rasmussen | |

FOREIGN PATENT DOCUMENTS

| | | | |
|---|---|---|---|
| JP | 2005-152451 A | 6/2005 | |
| JP | 2008-032689 A | 2/2008 | |
| WO | WO 2004-075932 | 9/2004 | |
| WO | WO-2014159696 A1 * | 10/2014 | A61L 2/07 |
| WO | WO 2016-164329 | 10/2016 | |
| WO | WO 2017-184444 | 10/2017 | |
| WO | WO 2017-192305 | 11/2017 | |
| WO | WO 2017-192306 | 11/2017 | |

OTHER PUBLICATIONS

Supplemental Partial European Search Report, EP17878809.7, dated Sep. 7, 2020, 3 pages.

* cited by examiner

PROCESS MONITORING DEVICE

CROSS REFERENCE TO RELATED APPLICATIONS

This application is a national stage filing under 35 U.S.C. 371 of PCT/US2017/065009, filed Dec. 7, 2019, which claims the benefit of U.S. Provisional Application No. 62/431,562, filed Dec. 8, 2016, the disclosure of which is incorporated by reference in its entirety herein.

BACKGROUND

The present disclosure relates to methods and articles of disinfecting medical devices using liquid disinfectant. Reusable medical devices or items that touch mucous membranes are commonly used in the medical arts. Examples of such devices include reusable flexible endoscopes, endotracheal tubes, anesthesia breathing circuits, and respiratory therapy equipment. When inserted into the body, these medical devices may become heavily contaminated with patient biomaterial and microorganisms, including potential pathogens. Careful reprocessing of the medical devices is critical to reducing the risk of cross-contamination and the possible transmission of pathogens between patients.

Flexible endoscopes are rated as semi-critical according to the Spaulding classification for medical devices, and therefore it is required that these devices be decontaminated by high level disinfection. Thus, it is recommended that both endoscopes and reusable accessories be frequently visually inspected in the course of their use and reprocessed, including before, during and after use, as well as after cleaning and before high-level disinfection. However, a visually based method of verification has severe limitations when applied to flexible endoscopes because the complex, narrow lumens in these devices cannot be directly visually inspected.

Automated endoscope reprocessors (AERs) are used to clean and disinfect flexible endoscopes to a level that mitigates transmission of pathogenic organisms and disease between patients who are subject to an endoscopic procedure. To disinfect AERs, a liquid disinfectant is typically recirculated through the AER for a prescribed time. Typically, the only information available to a user is the parametric information provided by the AER equipment itself which consists primarily of time and temperature information. The AER does not typically monitor chemically-related parameters capable of establishing the efficacy of the disinfection cycle. The AER also does not typically provide feedback on the how the disinfectant flows out of a medical device.

Some solutions provide for various process indicators to use with an AER, however, the process indicator does not necessarily provide details on the flow of liquid disinfectant which can be used to diagnose issues with the AER.

SUMMARY

Aspects of the present disclosure relate to articles that provide visual feedback of how a disinfectant outflows from a medical device.

In particular, aspects of the present disclosure relate to an article for detecting a disinfectant. The article can have a first substrate. The first substrate can have a first major surface and opposite ends. The article also can have a process indicator. The process indicator is disposed on at least a portion of the first major surface. The process indicator reacts with at least one liquid disinfectant selected from the group consisting of glutaraldehyde, ortho-phthalaldehyde, hydrogen peroxide, and peroxyacetic acid. The article can have a flow channel that is formed by a portion of the process indicator and that extends between the opposite ends.

The present disclosure can relate to a kit containing the article as well as a method of using the article in a disinfection process.

DETAILED DESCRIPTION

Aspects of the present disclosure relate to a flow channel formed from at least a portion of the process indicator.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports, and couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "front", "rear", "top", "bottom" and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

Throughout this disclosure, although disclosed as separate embodiments, the components of embodiments of FIGS. 1-10 can be similarly numbered unless otherwise indicated.

Figure 1A:
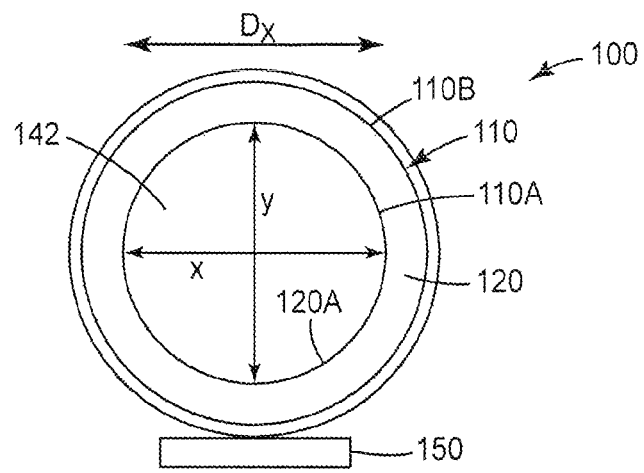
FIG. 1A is a front cross-sectional view of an article with a first substrate and a flow channel extending longitudinally therethrough.
Figure 1B:
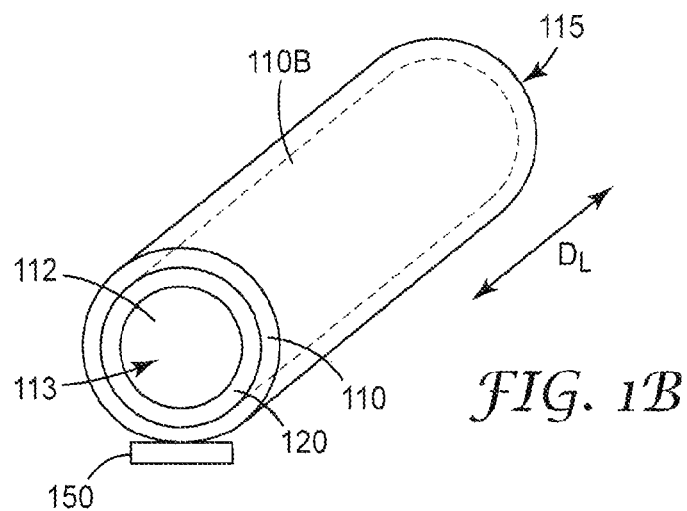
FIG. 1B is a front perspective view of the article of FIG. 1A.
Figure 1C:
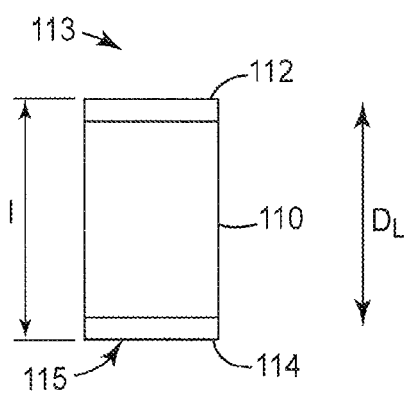
FIG. 1C is a side view the article of FIGS. 1A-1B.

FIGS. 1A-1C illustrates an exemplary embodiment of an article 100. The article 100 can perform disinfection indication of a disinfection process. The article 100 can have substrate 110 and a process indicator 120 which further defines a flow channel 142 extending longitudinally thereto.

The process indicator 120 can be disposed (e.g., as a thin film or coating) on a substrate 110. The process indicator 120 can be applied to the substrate by a suitable method described herein including, for example, spin coating, dip coating, spraying, brushing, roll coating, gravure coating, curtain coating, knife coating, and slot coating.

Preferably, the substrate 110 is selected to be unreactive with the disinfectant. The substrate may be porous or impermeable, and/or opaque or transparent, for example, but preferably transparent. Examples of suitable substrates include paper, metal, glass, and/or plastic/polymers sheets, films, membranes, fabrics (e.g., nonwoven, or woven), and combinations thereof.

Suitable polymeric materials include, but are not limited to, polyolefins, poly(isoprenes), poly(butadienes), polyurethanes, silicones, polystyrene, fluorinated polymers, chlorinated polymers, polyesters, polyamides, acrylic, polyimides, polyethers, poly(ether sulfones), poly(sulfones), polyphenylene oxides, poly(vinyl acetates), copolymers of vinyl acetate, poly(phosphazenes), poly(vinyl esters), poly(vinyl ethers), poly(vinyl alcohols), and poly(carbonates).

Suitable polyolefins include, but are not limited to, polyethylene terephthalate, poly(ethylene), poly(propylene), poly(1-butene), copolymers of ethylene and propylene, alpha olefin copolymers (such as copolymers of 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly(imino(1-oxohexamethylene)), poly(iminoadipoyliminohexamethylene), poly(iminoadipoyliminodecamethylene), and polycaprolactam. Suitable polyimides include, but are not limited to, poly(pyromellitimide). Suitable poly(ether sulfones) include, but are not limited to, poly(diphenylether sulfone) and poly(diphenylsulfone-co-diphenylene oxide sulfone). Suitable copolymers of vinyl acetate include, but are not limited to, poly(ethylene-co-vinyl acetate) and such copolymers in which at least some of the acetate groups have been hydrolyzed to afford various poly(vinyl alcohols). In some embodiments, cellulosic paper may be used, alone, or in combination with film or membranes of the foregoing polymeric materials. The selection of substrate 110 may be influenced by the process indicator 120 and is described further herein.

In some embodiments, the process indicator 120 can form a layer. The layer can be continuous across the surface of the substrate 110 and can have a uniform thickness. In other embodiments, the process indicator 120 forms one or more non-uniform deposits. In general, the type, thickness or uniformity of the process indicator 120 is not particularly important. It is preferable that a sufficient amount of the process indicator substance is present such that facile and accurate observation of the reacted process indicator composition with a disinfectant can be performed.

The process indicator 120 can be any disinfectant specific composition that reacts (either directly or indirectly) with at least one liquid disinfectant selected from the group consisting of glutaraldehyde, ortho-phthalaldehyde, hydrogen peroxide, and peroxyacetic acid. Some examples include sodium sulfite, ammonium chloride, ammonium bromide, ammonium bicarbonate, or ammonium acetate to indicate the presence of glutaraldehyde. A composition with an aldehyde-reactive group (such as the synthetic amine-containing compound described herein) to indicate the presence of ortho-phthalaldehyde Various compositions to indicate the presence of hydrogen peroxide or peroxyacetic acid are provided for example in U.S. Pat. Nos. 7,481,975, 7,670,552, and 6,566,090.

In some embodiments, the reaction of the composition with liquid disinfectant produces a visual indication of the presence of the liquid disinfectant. The composition can also indicate the concentration strength of the disinfectant in the liquid.

The process indicator 120 can be formed from a synthetic amine-containing polymer such as that described U.S. Application Nos. 62/332,243, filed May 5, 2016 and 62/332,255, filed May 5, 2016, which is incorporated herein by reference in its entirety.

In at least one embodiment, the process indicator 120 relies at least in part on the reaction of aldehyde in the disinfectant with one or more synthetic amine-containing compounds. In some exemplary embodiments, the synthetic amine-containing compound comprises at least one synthetic amine-containing polymer. In some preferred embodiments, the synthetic amine-containing polymer is derived from Polyethylenimine (PEI).

PEI is available in several forms such as linear, branched, and dendrimeric. Linear PEI can be represented by Formula I, below:

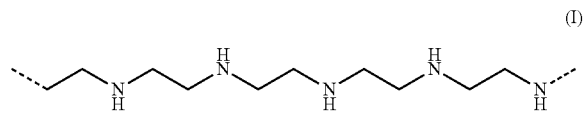

wherein - - - indicates continued linear polymeric ethylenimine-derived units or H. Linear PEI is available by post-modification of other polymers like poly(2-oxazolines) or N-substituted aziridines. Linear PEIs are commercially available and/or can be made according to known methods.

An exemplary branched PEI fragment can be represented by Formula II, below:

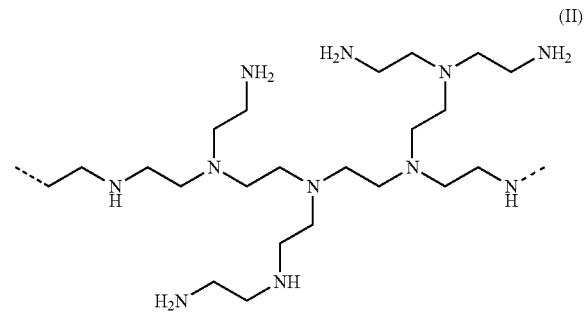

wherein - - - indicates continued linear and/or branched polymeric ethylenimine-derived units or H. As branching is typically more or less random, branched PEIs typically contain many compounds of this general type as a mixture. Branched PEI can be synthesized by the ring opening polymerization of aziridine. Branched PEIs are commercially available and/or can be made according to known methods.

Dendrimeric PEI is a special case of a branched PEI. An exemplary (generation 4) dendrimeric PEI is represented by Formula III, below:

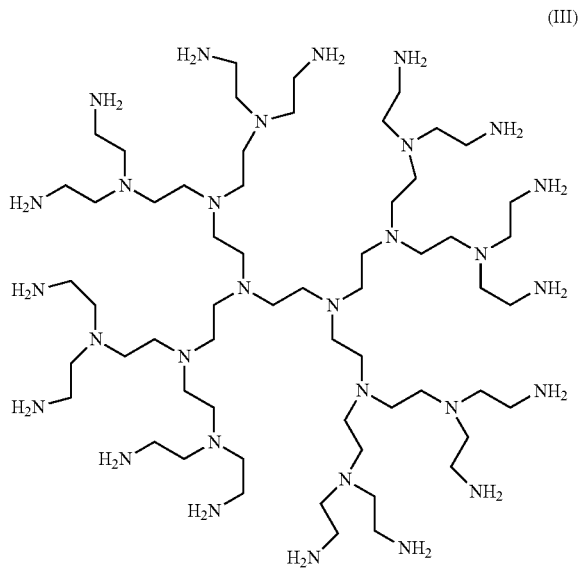 [SMILES: NCCN(CCN)CCN(CCN(CCN)CCN)CCN(CCN(CCN(CCN)CCN)CCN(CCN)CCN)CCN(CCN(CCN(CCN)CCN)CCN(CCN)CCN)CCN(CCN(CCN)CCN)CCN(CCN)CCN]

(III)

In this case, the PEI contains only primary and tertiary amino groups. Dendrimeric PEIs are commercially available and/or can be made according to known methods.

For the purposes of this application, the term "polyethylenimine" also includes ethoxylated polyethylenimine, which can be formed by reaction of some or all (preferably less than 50 percent, less than 30 percent, or even less than 10 percent) of the primary amino groups with one or more molecules of ethylene oxide. As used herein, the term "polyethylenimine" also includes protonated forms.

In one embodiment, the process indicator comprises, consists essentially of, or even consists of, at least one branched PEI. While such embodiments can be effective as indicators, there may be a tendency of the branched PEI to leach into the disinfectant. For this reason, it may be desirable to reduce the leaching rate of the PEI. This embodiment may be useful, for example, if glutaraldehyde is used in the disinfectant, since glutaraldehyde, which is a dialdehyde, may effect crosslinking of the branched PEI when it reacts with the primary amino groups.

In another embodiment, leaching is reduced or eliminated by e-beam grafting the branched PEI to a first substrate 110 on which it is disposed. In one method, the substrate 110 is contacted with PEI and exposed to e-beam radiation sufficient to cause grafting. Electron beam generators are commercially available from a variety of sources, including the ESI "ELECTROCURE" EB SYSTEM from Energy Sciences, Inc. (Wilmington, Mass.), and the BROADBEAM EB PROCESSOR from PCT Engineered Systems, LLC (Davenport, Iowa). For any given piece of equipment and irradiation sample location, the dosage delivered can be measured in accordance with ASTM E-1275 entitled "Practice for Use of a Radiochromic Film Dosimetry System". By altering extractor grid voltage, beam diameter and/or distance to the source, various dose rates can be obtained. Exemplary e-beam doses may be from about 5 kilograys (kGys) to about 100 kGys, at an accelerating voltage of 150 to 400 keV, preferably 250 to 350 keV. E-beam grafting can also be accomplished by methods such as, for example, those described in U.S. Pat. No. 8,551,894 (Seshadri et al.), wherein an amine-reactive ligand (e.g., a bromine atom or an acryloxy group) is grafted onto the substrate 110, and then the resulting functionalized substrate is contacted with PEI resulting in a chemical reaction that bonds the PEI to the substrate 110. Further details concerning e-beam grafting of PEI to a substrate 110 can be found in U.S. Pat. Appl. Publ. No. 2007/0154703 (Waller et al.). Suitable substrates are preferably porous, although this is not a requirement.

Leaching can be reduced also by washing the PEI-coating (e.g., 120) and the substrate 110 during manufacture so that the PEI-coated substrate 110 does not contain extraneous PEI that can leach into the AER disinfectant or rinse solutions.

The molecular weight of the PEI may be tailored depending on specific application requirements. In some embodiments, the PEI has a number average molecular weight ($M_w$) of at least 500 g/mole, at least 1500 g/mole, at least 2000 g/mole, at least 5000 g/mole, at least 15000 g/mole, at least 30000 g/mole, at least 60000 g/mole, or at least 100000 g/mole.

Exemplary substrates for e-beam grafting include porous membranes, porous nonwoven webs, papers, and porous fibers. In some embodiments, the polyethylenimine is crosslinked prior to reaction with the amine-reactive hydrolyzable organosilane (using a chemical crosslinker). Suitable crosslinkers have a plurality (e.g., 2, 3, 4, or 5) of amine-reactive groups that form covalent bonds to the amino groups. Preferably, the crosslinker has two amine reactive groups. Typically, crosslinking is affected by simply combining the PEI and the crosslinker under relatively high dilution conditions (favoring intramolecular crosslinking) to minimize gelation caused by interchain crosslinking. Determination of appropriate conditions is within the capabilities of those skilled in the art.

Examples of suitable crosslinkers may include crosslinkers represented by the formula $$R^3-Z-R^3$$

$R^3$ represents an amine-reactive group containing 1 to 12 carbon atoms. Preferably, $R^3$ contains 1 to 8 carbon atoms, more preferably 1 to 6 carbon atoms, and even more preferably 1 to 3 carbon atoms.

Exemplary amine-reactive groups $R^3$ include an isocvanato group (—N=C=O), an oxiranyl group

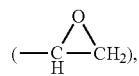

a glycidoxy group

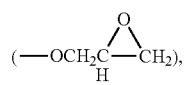

an acryl group

(—CCH=CH$_2$), an acryloxy group

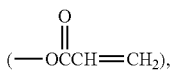
(—OCCH=CH$_2$), carboalkoxy groups having from 2 to 5 carbon atoms (e.g., carboethoxy group

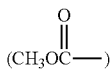
(CH$_3$OC—)

or a carbomethoxy group

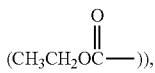
(CH$_3$CH$_2$OC—)), a vinylsulfonyl group

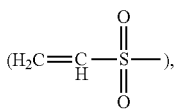
(H$_2$C=C(H)—S(O)$_2$—), cyclic anhydride groups

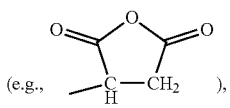
(e.g., )

alkylcarbamato groups

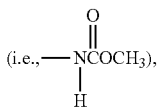
(i.e., —N(H)COCH$_3$), haloalkyl groups (e.g., BrCH$_2$— or ClCH$_2$—), and acrylamido groups

(i.e., —NHCCH=CH$_2$).

Z represents a divalent organic group containing 1 to 8 carbon atoms. In some embodiments, Z further contains from 1 to 6 heteroatoms selected from the group consisting of O, N, and S.

Suitable divalent organic groups Z include, for example: hydrocarbylene groups having 1 to 8 carbon atoms, more preferably 1 to 6 carbon atoms, more preferably 1 to 4 carbon atoms, and even more preferably 1 to 3 carbon atoms; alkylenoxyalkylene having 1 to 8 carbon atoms, more preferably 1 to 6 carbon atoms, more preferably 1 to 4 carbon atoms; di(alkylene)amino groups having 1 to 8 carbon atoms, more preferably 1 to 6 carbon atoms, more preferably 1 to 4 carbon atoms; alkylenethiaalkylene groups having 1 to 8 carbon atoms, more preferably 1 to 6 carbon atoms, more preferably 1 to 4 carbon atoms.

Specific examples of groups Z include methylene, ethylene, 1,2- and 1,3-propylene, butylene, isobutylene, hexylene, octylene, ethylcyclohexane-4,2'-diyl, ethylenoxyethylene, ethylenaminoethylene, ethylenoxypropylene, ethylenethiaethylene, and ethylene(methyl) aminoethylene. Of these, ethylene and 1,3-propylene are particularly preferred.

Suitable crosslinkers for PEIs include, for example, polyfunctional compounds such as: halohydrins (e.g., epichlorohydrin); polyfunctional acrylates (e.g., 1,6-hexanediol diacrylate, ethylene glycol diacrylate, diethylene glycol diacrylate, triethylene glycol diacrylate, tetraethylene glycol diacrylate, ethoxylated trimethylolpropane triacrylates, trimethylolpropane triacrylate, glycerol triacrylate, dipentaerythritol hexaacrylate); dialdehydes (e.g., alkyl, aryl or alkaryl dialdehydes such as oxaldehyde, malondialdehyde, propanedialdehyde, succinaldehyde, glutaraldehyde, adipaldehyde, 2-hydroxy-hexanedial, phthalaldehyde, 1,4-benzenediacetaldehyde, 4,4-(ethylenedioxy)dibenzaldehyde, and 2,6-naphthalenedialdehyde); diepoxides (e.g., aliphatic, cycloaliphatic and glycidyl ether diepoxides such as, for example, vinylcyclohexene dioxide, 3,4-epoxycyclohexylmethyl 3,4-epoxycyclohexanecarboxylate, 3,4-epoxy-6-methylcyclohexylmethyl 3,4-epoxy-6-methylcyclohexanecarboxylate, bis(3,4-epoxy-6-methylcyclohexylmethyl) adipate, dipentene dioxide, diglycidyl ether of bis-phenol A, diglycidyl ether of bis-phenol F, 1,4-butanediol diglycidyl ether); diesters (e.g., diethyl adipate, dimethyl fumarate, diethyl sebacate, and dimethyl maleate); divinylsulfone; polyfunctional acrylamides (e.g., piperazine diacrylamide, diacrylamide, N,N-methylene diacrylamide, and N,N'-(ethane-1,2-diyl)diacrylamide); polyisocyanates (e.g., hexamethylene diisocyanate, methylene diisocyanate), and polyaziridinyl compounds (e.g., tris-(1-aziridinyl)phosphine oxide), carbodiimides (e.g., 1-ethyl-3-(3-dimethylaminopropyl) carbodiimide), and N-hydroxysuccinimide. Additional crosslinkers are known in the art, and will be available to those of skill in the art.

Preferably, an amount of the crosslinker is used that results in reaction with from 1 to 10 percent of the available primary nitrogen atoms in the PEI, more preferably 3 to 8 percent.

In some embodiments, an increase in the ratio of secondary to primary amines results in a different contrast in color or other spectral measurement. For example, the ratio of secondary to primary amines in the branched or dendrimetric PEI may be at least 1:1, at least 3:1, at least 5:1, or even at least 10:1.

The crosslinker is used in considerably less than equivalent quantity (or stoichiometric ratio) with respect to the primary and/or secondary amino groups. The crosslinker quantity can leave at least one fourth, or even at least one-half of the NH groups in the polymer unreacted. If desired, an excess of unreacted PEI may be added to the solution of partially crosslinked polymeric reaction product to increase the overall average frequency of unreacted NH groups.

In another embodiment, the process indicator comprises, consists essentially of, or consists of at least one crosslinked branched guanylated PEI. Guanylated PEIs can be made using a guanylating agent, for example, according to the procedures described in U.S. Pat. Appl. Publ. No. 2016/0096802 (Rasmussen et al.). As used herein, the term "guanylating agent" means a compound that is reactive with an amino moiety of an amine compound to provide a guanidino-functional compound (e.g., reaction of the guanylating agent with the amino moiety can form a guanidino moiety in situ through an addition reaction or a displacement reaction).

Exemplary guanylating agents include O-alkylisourea salts, S-alkylisothiourea salts, carbodiimides, cyanamides, amidino-functional salts, and combinations thereof. Preferred guanylating agents include O-alkylisourea salts, carbodiimides, and combinations thereof. Representative examples of suitable guanylating agents that can react with amines through displacement reactions include O-methylisourea sulfate (also known as O-methylisourea hemisulfate), O-methylisourea hydrogen sulfate, O-methylisourea acetate, O-ethylisourea hydrogen sulfate, O-ethylisourea hydrogen chloride, S-methylisothiourea sulfate (also known as S-methylisothiourea hemisulfate), S-methylisothiourea hydrogen sulfate, S-methylisothiourea acetate, S-ethylisothiourea hydrogen sulfate, S-ethylisothiourea hydrogen chloride, chloroformamidine hydrochloride, 1-amidino-1,2,4-triazole hydrochloride, 3,5-dimethylpyrazole-1-carboxamidine nitrate, pyrazole-1-carboxamidine hydrochloride, N-amidinopyrazole-1-carboxamidine hydrochloride, and combinations thereof. Representative examples of suitable guanylating agents that can react with amines through addition reactions include dicyclohexylcarbodiimide, N-ethyl-N'-(3-dimethylaminopropyl)carbodiimide, diisopropylcarbodiimide, diphenylcarbodiimide, cyanamide, and combinations thereof.

Preferred guanylating agents include O-methylisourea sulfate, O-methylisourea hydrogen sulfate, O-methylisourea acetate, O-ethylisourea hydrogen sulfate, O-ethylisourea hydrogen chloride, dicyclohexylcarbodiimide, N-ethyl-N'-(3-dimethylaminopropyl)carbodiimide, diisopropylcarbodiimide, diphenylcarbodiimide, and combinations thereof. Particularly preferred guanylating agents include O-methylisourea sulfate, O-methylisourea acetate, diisopropylcarbodiimide, and combinations thereof. Such guanylating agents are known and can be prepared by known methods. At least some of the guanylating agents are also commercially available.

In another embodiment, the process indicator may comprise, consist essentially of, or even consist of, a crosslinked silylated branched polyethylenimine. Branched silylated polyethylenimine can be prepared, for example, by reaction of an amine-reactive organosilane coupling agent with at least some of the primary amines present in branched PEI resulting in silylated branched PEI. Examples of suitable amine-reactive organosilane coupling agents include compounds represented by the formula:

$$R^3 \text{---} Z \text{---} SiY_3$$

wherein $R^3$ and $Z$ are as previously defined, each $Y$ independently represents a hydrolyzable group.

The term "hydrolyzable group", as used herein, denotes a group that can be hydrolyzed, which means it can react with water to provide silanol groups (Si—OH groups) that can further react with groups (e.g., hydroxyl groups) on the surface of the substrate 110. The hydrolysis and condensation reactions may occur spontaneously and/or in the presence of a hydrolysis/condensation catalyst. Examples of hydrolyzable groups include halide groups, such as chlorine, bromine, iodine or fluorine, alkoxy groups (—OR' wherein R' represents an alkyl group, preferably containing 1 to 6, more preferably 1 to 4 carbon atoms, and which may optionally be substituted by one or more halogen atoms), acyloxy groups (—O—(C=O)—R" wherein R" is as defined for R'), aryloxy groups (—OR''' wherein R''' represents an aryl moiety, preferably containing 6 to 12, more preferably containing 6 to 10 carbon atoms, which may be optionally substituted by one or more substituents independently selected from halogens and $C_1$-$C_4$ alkyl groups which may optionally be substituted by one or more halogen atoms). In the above formulae, R', R", and R' may include branched structures.

In some preferred embodiments, each Y is independently selected from methoxy, ethoxy, hydroxy, acetoxy, chlorine, and bromine, of which methoxy and ethoxy are particularly preferred.

Examples of suitable amine-reactive organosilane coupling agents include: 3-isocyanatopropyltriethoxysilane; 3-isocyanatopropyltrimethoxysilane; 2-isocyanatoethyltriethoxysilane; 2-isocyanatoethyltrimethoxysilane; 3-acryloxypropyltriethoxysilane; 3-acryloxypropyltrimethoxysilane; 2-acryloxyethyltriethoxysilane; 2-acryloxyethyltrimethoxysilane; 2,3-epoxypropyltrimethoxysilane; 2,3-epoxypropyltriethoxysilane; 3-glycidoxypropyltriethoxysilane; 3-glycidoxypropyltrimethoxysilane; 2-(3,4-epoxycyclohexyl)ethyltrimethoxysilane; and 2-(3,4-epoxycyclohexyl)ethyltriethoxysilane.

Suitable amine-reactive hydrolyzable organosilanes may be purchased from commercial sources (e.g., as silane coupling agents, for example, from Gelest, Inc., Morrisville, Pa.) and/or can be prepared by known methods. Preferably, the amine-reactive hydrolyzable organosilanes are reactive with primary amino groups, and optionally with secondary and/or tertiary amino groups. Preferably, the amine-reactive hydrolyzable organosilanes react more rapidly with primary amino groups than secondary and tertiary groups (if at all).

In this embodiment, typically, from 5 to 70 percent of the primary amino groups, preferably 10 to 40 percent of the primary amino groups, in the PEI are reacted with the silane coupling agent. The reaction is typically carried out in an organic solvent, although water may be present if desired. Upon coating and drying of the silane-functionalized PEI on a substrate 110, the hydrolyzable groups hydrolyze and form siloxane crosslinks to other silane groups. This results in a crosslinked PEI disposed on the substrate 110, and depending on the substrate 110, it may be chemically bonded to the substrate 110 (e.g., if the substrate has available hydroxyl groups at its surface; e.g., as in the case of cellulosic paper). Exemplary substrates may include any substrate described herein.

In another embodiment, the synthetic amine-containing compound comprises a polyethylenimine that is chemically bonded to silica. This may be achieved, for example, by coating an acidified dispersion of silica nanoparticles on a substrate 110 (e.g., cellulosic paper or a substrate as described elsewhere herein), drying to form a silica coating on the substrate. Contacting the silica surface (e.g., by dip coating, spraying, or spin coating) with an amine-reactive silane coupling agent (e.g., 3-acryloxypropyltrimethoxysilane or 3-isocyanatopropyltriethoxyilane or other coupling agents as described herein) cause reaction and functionalization of the silica with amine-reactive groups on its surface.

Subsequently contacting the functionalized surface with PEI results in covalent bonding of the PEI to the silica, thereby reducing leaching into recirculating disinfectant. Further details concerning the preparation of acidified silica nanoparticle dispersions and acid-sintered silica coatings prepared thereby can be found, for example, in U.S. Pat. Appl. Publ. Nos. 2015/0232673 (Jing et al.), 2015/0203790 (Strerath et al.), 2015/0252196 (Strerath et al.), and 2015/0246350 (Sun et al.).

Polyethylenimine that is chemically bonded to silica can also be prepared by a multi-step process in which silica particles (e.g., colloidal silica particles) are combined with an amino-functional hydrolyzable silane (e.g., aminopropyltriethoxysilane, aminopropyltrimethoxysilane). The resulting dispersion of amino-functional silica particles is mixed with a second dispersion of a silylated branched polyethylenimine (e.g., preparable as discussed hereinabove). The resulting mixture is then coated onto a substrate 110 and dried.

If desired, polyallylamine (PAA) may be substituted for, or combined with, polyethylenimine in the various embodiments described herein. Polyallylamine can be obtained from commercial sources (e.g., Sigma-Aldrich Corp.) or prepared according to known methods.

The molecular weight of the PAA may be tailored depending on specific application requirements. In some embodiments, the PAA has a number average molecular weight ($M_w$) of at least 500 g/mole, at least 5000 g/mole, at least 15000 g/mole, at least 30000 g/mole, at least 60000 g/mole, or at least 100000 g/mole.

A process indicator 120 can be applied using a composition. The composition preferably comprises a liquid vehicle, which may be organic and/or aqueous, although this is not a requirement. If present, the liquid vehicle should generally be chosen to minimize reaction between them and other components of the composition. Examples of organic vehicles include alcohols and ethers. Examples of aqueous liquid vehicles include water and water-alcohol mixtures (e.g., water-isopropanol mixtures). If a liquid vehicle is present, the other ingredients are preferably dissolved of dispersed in it. Any amount of the liquid vehicle can be used, and will typically depend on the particular composition and/or intended use.

Optionally, the composition may further comprise a polymeric binder. In embodiments wherein a liquid vehicle is present, the additional polymeric binder is preferably dispersible or soluble in the liquid vehicle. Exemplary additional polymeric binders include water-soluble polymers such as, for example, polyvinyl alcohol, hydroxyethyl cellulose, hydroxypropyl cellulose, and polymer latexes (e.g., polyurethane latexes, acrylic latexes, and vinyl acetate latexes).

Suitable polymeric binders include film-forming polymeric binders, which may be provided, for example, as a latex. In some preferred embodiments, the latex is added to the composition prior to depositing the composition on a substrate 110. Suitable film-forming polymers include acrylics (e.g., polybutyl acrylate and polymethyl methacrylate), ethylene-vinyl acetate copolymers (and partially or completely hydrolyzed versions thereof, polyvinyl alcohols, polyurethanes, polyamides, polyvinyl chloride, polystyrenes, polyesters, polycarbonates, natural and synthetic rubbers, and combinations thereof. The film-forming polymeric binder may be self-crosslinkable.

If present, the film-forming polymeric binder is preferably present in an amount of up to 50 percent by weight, more preferably from 1 to 30 percent by weight, and more preferably from 5 to 25 percent by weight, based on the combined total weight of the film-forming polymeric binder and the synthetic amine-containing compound(s).

The composition may optionally further comprise various additives such as, for example, thickeners, fillers, fragrances, antioxidants, UV stabilizers, and surfactants.

Compositions according to the present disclosure can typically be prepared by simply mixing the various components in a vessel, optionally with heating or cooling.

Compositions according to the present disclosure are useful, for example, for method of making an article 100 by coating at least a portion of a first major surface 110A of a substrate 110 with the composition, and then hydrolyzing at least some of the hydrolyzable groups to forms form covalent crosslinks (e.g., having Si—O—Si units) between PEI chains and/or the substrate. Hydrolysis may occur spontaneously on drying or standing. Optional heating may be advantageous in some instances.

Various constructions of an article 100 are possible. In FIG. 1A, an article 100 with a circular cross-section is shown. The width of the article 100 can be provided by the diameter which is an end to end measurement along the lateral axis Dx. The substrate 110 can have a first major surface 110A and a second major surface 110B. The process indicator 120 can be disposed on at least a portion of the first major surface 110A forming a channel 142 therein. In some embodiments, the process indicator 120 is disposed on the entire first major surface 110A which can include the entire circumference of a portion of the article 100. In some embodiment, the process indicator 120 is disposed on the entire length of the first substrate along the longitudinal axis DL (as shown in FIG. 1B) and a portion of the circumference of the article 100.

The second major surface 110B can form an outer portion of the article 110 and may be exposed to an environment of a disinfection system.

The first substrate 110 can have ends 113 and 115 shown in FIGS. 1B and 1C. As discussed herein, the first substrate 110 can have a process indicator 120 disposed thereon over all or a portion of the surface 110A. A flow channel 142 can be established between the ends 113 and 115 from at least a portion of the process indicator 120.

The flow channel 142 can be defined by at least a portion of the process indicator 120 and/or the first substrate 110 (e.g., the exposed portion of the substrate 110 or the portion with the process indicator 120 defined therein). For example, when the process indicator 120 is partially covering the first substrate 110, then the flow channel 142 could partially be defined by the first substrate 110 and the process indicator 120.

The flow channel 142 can have one or more walls. In the present embodiments, the flow channel 142 is shown having a single wall formed from a portion of the process indicator 120. The flow channel 142 can have a particular width x (measured along the lateral axis) and a particular height y (measured along an axis perpendicular to the lateral D. In article 100, the flow channel 142 can be measured by an inner diameter (i.e., x).

The flow channel 142 can be oriented along the longitudinal axis DL. For example, the flow channel 142 can extend in the longitudinal direction and is perpendicular to the lateral axis, D. The distance from end 113 to end 115 along the longitudinal axis is 1 (as shown in FIG. 1C).

Although various configurations of the flow channel 142 are possible, the flow channel generally has a width x that is no greater than its length 1. The flow channel 142 can also be cut and shaped according to the desired length. For example, the distance 1 between the ends 113, 115 may be no greater than 4 inches, no greater than 3 inches, no greater than 2 inches, no greater than 1 inch. In at least one embodiment, the width x of the flow channel 142 may be no greater than 0.5 inches, no greater than 0.375 inches, no greater than 0.25 inches, or no greater than 0.125 inches.

A disinfectant can flow through the flow channel 142 from the end 113 and to the end 115. The end 113 can have a first area and out thru the end 115 can have a second area (each defined by the flow channel). In some embodiments, the first area is larger than the second area in order to create a backpressure with the disinfectant flow. The backpressure can cause process indicator 120 to react to the presence of disinfectant more readily than without backpressure.

The backpressure can be achieved using multiple techniques. In some embodiments, the end 115 can be sealed. For example, the article 100 can be a sock-like contraption that is fitted adjacent or even around a tip of an endoscope.

FIG. 1C shows a membrane 112 and a membrane 114 covering at least a portion of the end 113 and end 115, respectively. The membranes can cover the area defined by the first area, second area, or both. Membrane 112 and membrane 114 can be optional. For example, the absence of the membrane 112 and presence of membrane 114 can create backpressure. The membrane 112 can also have a larger pore size than membrane 114 in order to create backpressure when disinfectant flows through end 113.

The article 100 can also include an adhesive 150 disposed on the second major surface 110B of the first substrate 110. The adhesive 150 can be disposed such that the article 100 adheres to a surface such as a surface found on an Automated Endoscope Reprocessor (AER). The adhesive 150 can be planar with an attachment surface. In some embodiments, the adhesive 150 can be a pressure-sensitive adhesive.

Figure 2A:
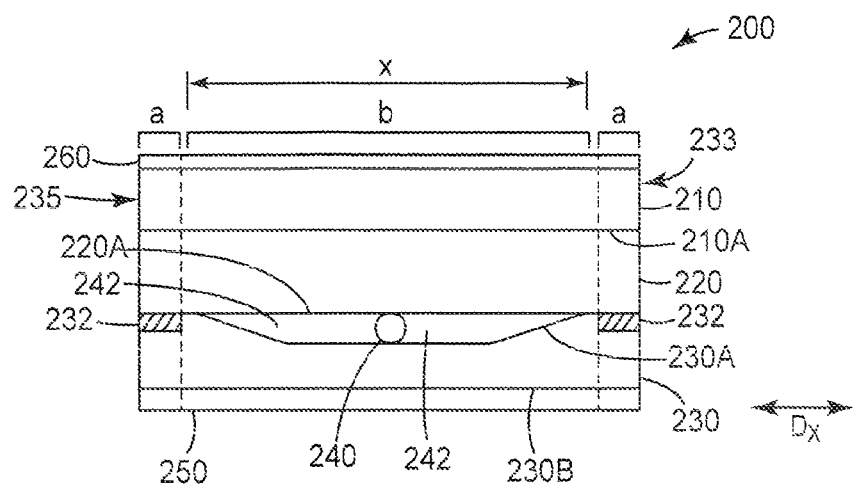
FIG. 2A is a front cross-sectional view of an article with a second substrate and a flow channel extending longitudinally therethrough.

FIG. 2A shows an article 200 that uses two substrates. The article 200 can have a first substrate 210 with a first major surface 210A and second major surface 210B. The first substrate 210 can be similar to that of the first substrate 110 in FIGS. 1A-1C.

The article 200 can also have a process indicator 220 that is disposed on at least a portion of the first major surface 210A. The process indicator 220 can have a first major surface 220A.

The first substrate 210 can further have at least one face. The first substrate 210 can have a longitudinal face (e.g., 233, or 235) and a lateral face. The longitudinal face (e.g., 233, or 235) can be defined by the face oriented along the longitudinal axis DL on a side of the article 200. For example, the longitudinal face can be also defined by the orientation of the flow channel 242. The length of longitudinal face (e.g., 233, or 235) can also be defined by the length 1 of the first substrate 210. The length of the first substrate 210 is the distance between a first lateral face and a second lateral face. The lateral face is defined by the face oriented along the lateral axis D.

The article 200 can also have a polymer film 260 disposed on the second major surface 210B. The polymer film 260 can form a protecting layer of the article 200. In some embodiments, the polymer film extends over the first substrate and the process indicator 220 along the longitudinal face (e.g., 233 or 235). The polymer film 260 can be any resilient polymer. In some embodiments, the polymer film can be a polyethylene terephthalate (PET) film. While the thickness can vary depending on the durability desired, the thickness of the PET film can be less than 10 thousandths of an inch. An adhesive can optionally be disposed between the second major surface 210B and the polymer film 260 in order to secure the polymer film 260 to the second major surface 210B.

The article 200 can have a second substrate 230 with a first major surface 230A and a second major surface 230B. The second substrate 230 can be used to form a flow channel 242 with the first major surface 210A. In particular, the first major surface 230A can form the flow channel 242 with the first major surface 220A. The second substrate 230 can be positioned such that process indicator 220 can be sandwiched between the first substrate 210 and the second substrate 230. The second substrate 230 can be attached to a surface by an adhesive 250.

To form the flow channel 242, the second substrate 230 can be attached to the first substrate 210 and/or the process indicator 220 in a position proximate the longitudinal face (e.g., 233, or 235). For example, the second substrate 230 can attach to an edge of the first substrate 210. The second substrate 230 can also contact at least a portion of the process indicator 220 during the attachment to the first substrate 210. Preferably, the second substrate 230 attaches to the first substrate 210 through a longitudinal edge region (described herein) of the first substrate. The longitudinal edge region can be an area of attachment. The longitudinal edge region can be where an attachment point can be formed with the second substrate 230 while still forming a flow channel 242. The flow channel width x can be measured based on the distance b while the longitudinal edge region can be defined by a distance of a.

An attachment can bond at least some of the layers of the article 200 (as shown in the adhesive 232 bonding the second substrate 230 to the process indicator 220). The attachment is shown by distance a which is the distance from the longitudinal face 233, 235 to the innermost portion of the attachment. In some embodiments, a is no greater than 80%, no greater than 60%, no greater than 50%, no greater than 40%, no greater than 30%, no greater than 20% of b. In some embodiments, a is no greater than 30%, no greater than 20%, no greater than 10%, no greater than 5% of the distance of a+b.

The attachment can be mechanical, adhesive, or bonding. If a narrower flow channel 242 is desired, then the attachment can attached away from the longitudinal face (increasing the distance a, decreasing the distance b).

Figure 2B:
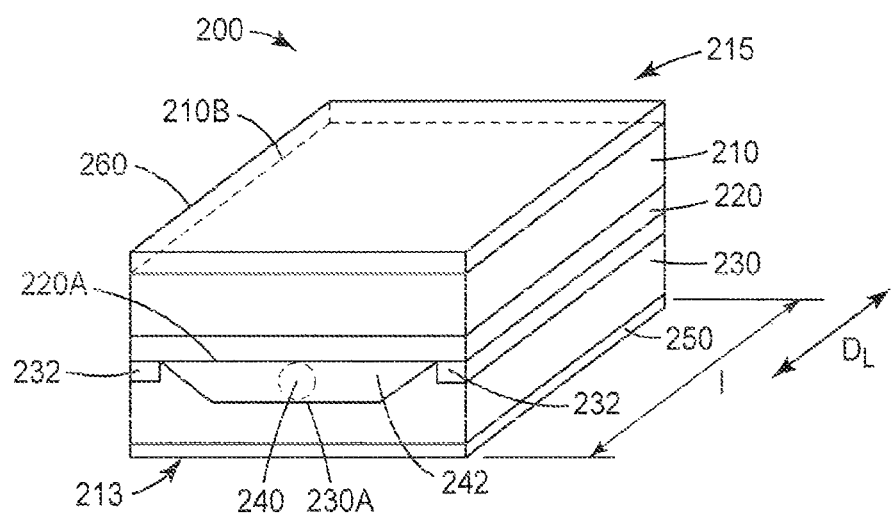
FIG. 2B is a front perspective view of the article of FIG. 2A.
Figure 3:
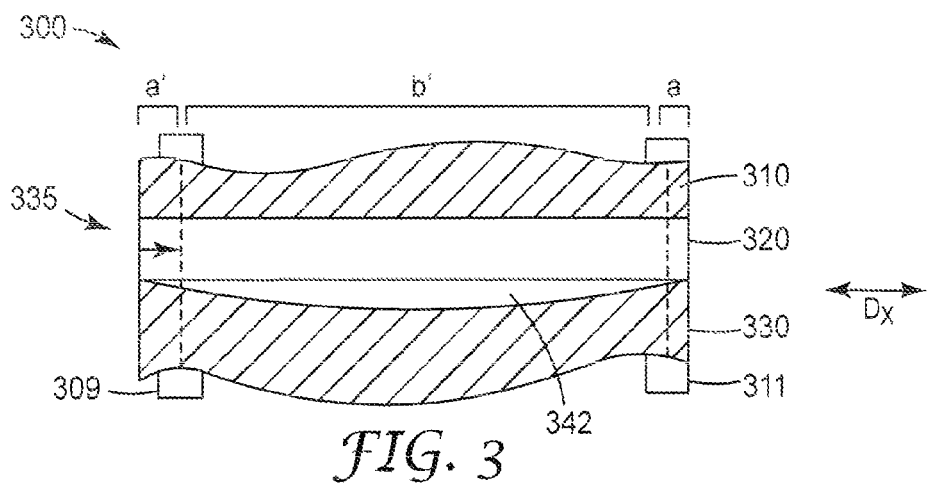
FIG. 3 is a front cross-sectional view of an article having a mechanical attachment.

FIG. 3 shows an article 300 of similar construction to the article 200 of FIGS. 2A-2B except that article 300 includes mechanical attachments 309 and 311. The attachment 309 being attached in a position further inward from a longitudinal face 335 (relative to article 200)(within the longitudinal edge portion). The distance a' can be greater than that of distance a in article 200 which decreases the flow channel width 342 defined by distance b'. The distance a is left unchanged from article 200. The two mechanical attachments penetrate through the layers (first substrate 310, process indicator 320, and second substrate 330). The mechanical attachments are pictured as rivets.

Returning to FIG. 2B, the flow channel 242 can be formed between ends 213 and 215 of the article 200. The article 200 shows flow channel 242 having at least two walls, one wall formed by major surface 220A and another wall formed by major surface 230A. The adhesive 232 may also form a side wall of the flow channel 242.

The article 200 can have features that promote the flow of disinfectant through the flow channel 242. For example, portions of the first major surface 210A and the first major surface 230A can be made either hydrophobic or hydrophilic to draw disinfectant into the process indicator 220. For example, the first major surface 230A can be hydrophobic and the first major surface 210A can by hydrophilic.

The article 200 can also include a spacing element 240. The spacing element 240 maintains the flow channel 242 by maintaining an opening for disinfectant to flow through the flow channel 242 (thus preventing collapse of the flow channel 242). The spacing element 240 can be a mechanical device that is integrated with or separate from any of the substrates. In FIG. 2A, the spacing element 240 is shown as a rigid tube inserted into the flow channel 242. In some embodiments, the spacing element forms at least a portion of the flow channel 242. The spacing element 240 can be generally sandwiched between the process indicator 220 and the second substrate 230. If a spacing element is present, then the height of the flow channel 242 can be defined by the spacing element 240.

The spacing element 240 can be formed from a variety of materials. For example, the spacing element 240 can be a tube which further has one or more openings formed from a body of the tube. In other examples, the spacing element 240 can also be a sponge or a non-woven polymer or foam.

As discussed herein, the spacing element 240 can also be integrated with the second substrate 230.

Figure 4A:
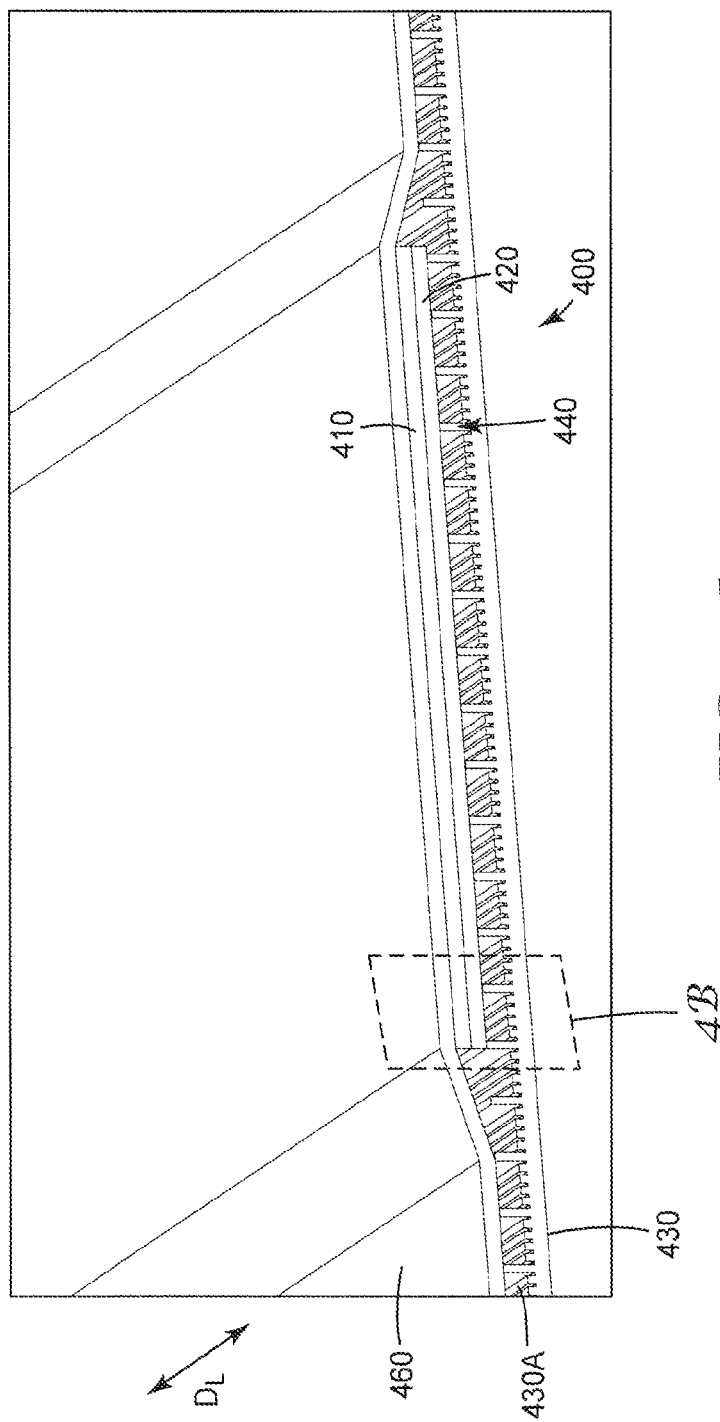
FIG. 4A is a front perspective view of an article having a plurality of flow channels.
Figure 4B:
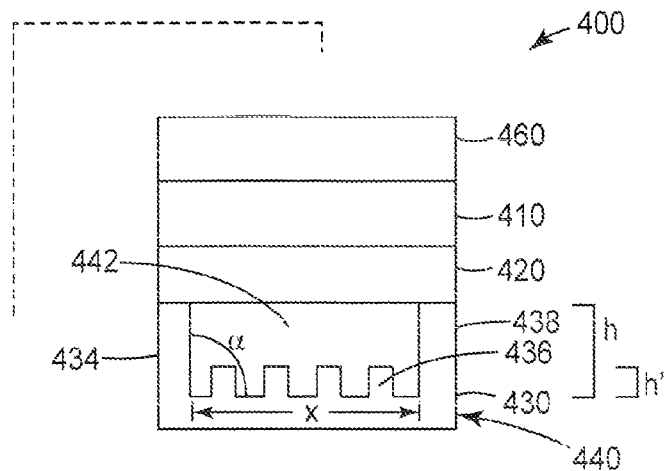
FIG. 4B is a side cross-sectional view of a section of the article in FIG. 4A.

FIGS. 4A-4B illustrate an article 400 with a spacing element 440 that is integrated into the second substrate 430. In some embodiments, the second substrate 430 can be a microreplicated surface such that the process indicator 420 forms at least one flow channel with the first major surface 430A.

As shown in FIG. 4B, the spacing element 440 can be a plurality of members. At least two of the members, 434, and 438 can be raised relative to the other members 436. At least one of the members, e.g., 434, extends through at least a portion of the length of the second substrate 430 along the longitudinal axis and is non planar to the second substrate 430. In some embodiments, the member 434 extends the entire length of the second substrate.

A surface of the member 434 is generally straight and positioned to form an angle α with a major surface 430A of the second substrate 430. The angle α can be from 1 to 179 degrees such that structural integrity of the flow channel is maintained. Preferably, angle α is about 90 degrees. The member 434 can have a height h which defines the flow channel 442 height. In some embodiments, the height can be at least 0.01 millimeter, at least 0.1 millimeter, or at least 0.5 millimeters.

Members 436 can have a height h' which is less than that of height h. In some embodiments, members 436 are optional and does not contribute to the flow channel height. However, additional disinfectant flow management may be affected by members 436. Members 436 can also extend at least a portion of the length of the second substrate 430 and is non-planar to the second substrate 430. In some embodiments, the member 436 is perpendicular to the second substrate 430.

The flow channel width can be provided by x which is including the distance between member 434 and 438. The members can be defined by a spacing between the members. For example, the distance from the member 436 and member 438 can be at least 0.2 millimeters.

In some embodiments, the member 438 can also have a portion that extends away from the member 438 and is parallel to the second substrate 430.

Figure 5:
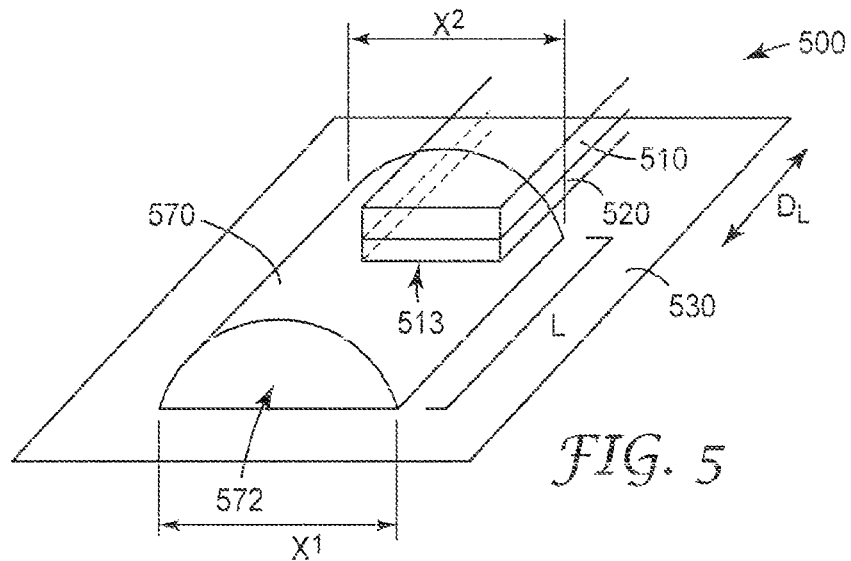
FIG. 5 is a front perspective view of any of the articles in FIGS. 2-4 with a funneling device.

FIG. 5 illustrates an article 500 with a funneling device 570. The article 500 can have a first substrate 510, and a process indicator 520 disposed thereon. The process indicator 520 can be at least partially disposed on the second substrate 530 forming a channel as described herein.

The funneling device 570 can be configured to direct disinfectant flow into the end 513 of one or more flow channels. For example, a first end 572 can receive the disinfectant flow and direct it toward the end 513. The funneling device 570 can have a sufficient height in order to fit over the first substrate 510. The funneling device 570 can have a first end 572 having a width $X^1$ and a second end having a width $X^2$. In at least one embodiment, the width $X^1$ is at least the width of $X^2$. The funneling device 570 can also have a length L. The length L can be modified depending on the degree of disinfectant flow desired.

Figure 6:
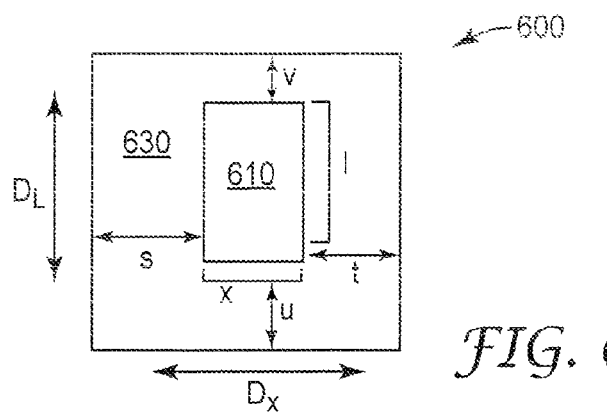
FIG. 6 is an elevational view of any of the articles in FIGS. 1-4.

In FIG. 6, the second substrate 630 can have a larger area than the first substrate 610. Not shown is the process indicator. The width and length of the article 600 may influence the pressure needed from an AER. Generally, the ratio of length to width of the process indicator portion (e.g., length L and width x) is no greater than 2:1, no greater than 3:1, no greater than 4:1.

Figure 7:
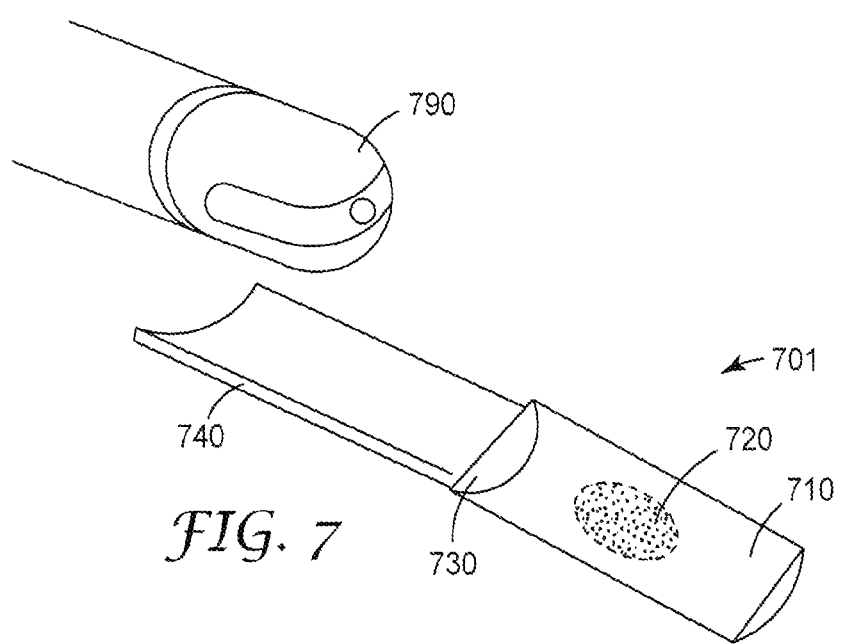
FIG. 7 is a front-side perspective view of an article with a spacing element.

In FIG. 7, an endoscope 790 is fitted into an article 701 of the present disclosure using a spacing element 740. The spacing element 740 can be substantially u-shaped to substantially conform to the endoscope 790 and is inserted into the article 701 (which is similar to that of article 200 in FIG. 2). The spacing element 740 can contact a second substrate 730. The spacing element 740 can be positioned between second substrate 730 and process indicator 720. The process indicator 720 can be deposited on a portion of the substrate 710. As illustrated, process indicator 720 is shown with the substrate 710 cut-away and is meant to be positioned in the interior of the article 701. The disinfectant can flow through the endoscope 790 and into the flow channel formed from the process indicator 720 and the second substrate. The disinfectant can contact the process indicator 720 which can provide a visual indication of the disinfection.

Figure 8:
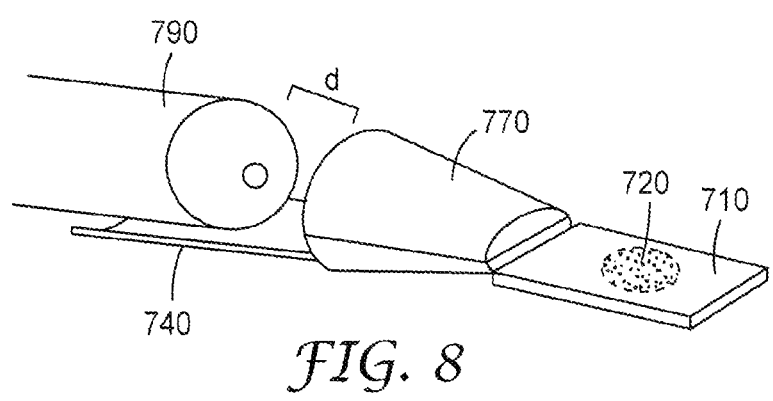
FIG. 8 is a front-side perspective view of an article with a spacing element and a funneling device.

In FIG. 8, an endoscope 790 is positioned to be resting on the spacing element 740. Outflow from the endoscope 790 can be concentrated into a funneling device 770. A stand-off distance d between the endoscope 790 tip and the funneling device 770 may be present. The disinfectant can flow from the endoscope 790 and into the funneling device 770. The funneling device 770 can concentrate the flow of the disinfectant through a flow channel as described in FIG. 7.

Figure 9:
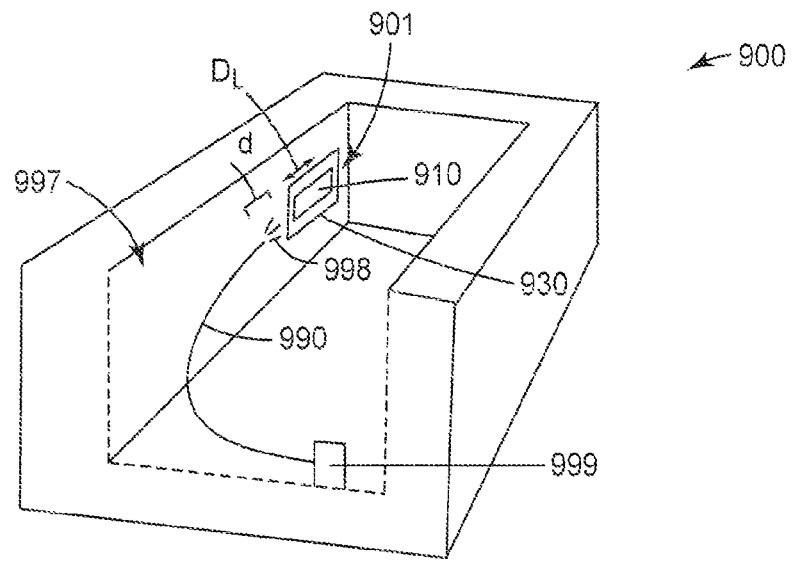
FIG. 9 is a front perspective view of a disinfection system.

FIG. 9 illustrates a perspective view of a disinfection device 900. The disinfection device 900 includes a basin 997 where the disinfection takes place. The disinfection device 900 can include a disinfectant port 999 where a medical device (e.g., an endoscope) 990 is attached. The medical device 990 can be positioned within the basin 997. When disinfectant flows through the disinfection port 999 and the medical device 990, an outflow 998 is produced at the end of the medical device 990. The outflow 998 collects in the basin 997. An article 901 is positioned within the basin 997 such that the article 901 can provide an indication of the outflow 998. The article 901 can be similar to that of the article from FIGS. 1-8.

The article 901 can be oriented along the longitudinal axis DL at a particular stand-off distance d from the outflow 998. For example, the article 901 can be positioned such that the standoff distance d between the outflow 998 of the medical device and the flow channel is no greater than 3 inches, no greater than 2 inches, no greater than 1 inch, or no greater than 0.5 inches.

The article 901 can be positioned such that at least a portion of the flow channel is oriented toward the outflow. For example, a majority of the flow channel can be oriented toward the outflow 998.

The disinfectant may comprise an aldehyde known for disinfecting medical equipment such as, for example, formaldehyde and dialdehydes (e.g., flutaraldehyde, glutaraldehyde or ortho-phthalaldehyde), and combinations thereof. The disinfectant may include the aldehyde(s) in a liquid vehicle such as, for example, water, organic solvent (e.g., propylene glycol), or a mixture thereof. Appropriate dilution levels may be dictated by industry and/or regulatory standards. When the concentration of the aldehyde in the disinfectant is sufficient, reaction of the aldehyde with the synthetic amine-containing compound results in products that may have a color and/or other spectral property (e.g., dielectric constant) change that can be readily observed.

Examples of suitable medical articles 990 for practicing the present disclosure include, for example, a grasper (e.g., forceps), a clamp, an occluder, a retractors, a distractor, a positioner, a stereotactic device, a mechanical cutter (e.g., a scalpel, a lancet, a rasp, a trocar, a drill bit, a rongeur, a reamer, a ridged reamer, a bone curette, a scissors, a broach), a dilator, a speculum, a sealing device (e.g., a surgical stapler), a needle (e.g., for irrigation or injection), a tip (e.g., for irrigation or suction), a tube (e.g., for irrigation or suction), a tool (e.g., a hip impactor, a screwdriver, a spreader, a hammer, a spreader brace, a probe, a carrier, an applier, a cutting laser guide, a ruler, a calipers, a drill key), a powered device (e.g., a dermatome, an ultrasonic tissue disruptor, a cryotome, a drill), and a lumened device. Lumened devices have at least one internal conduit through which the disinfectant may be introduced. Examples of lumened devices include endoscopes such as, for example, an arthroscope, a laparoscope, a thoracoscope, a cystoscope, a rhinoscope, a bronchoscope, a colonscope, a choledochoscope, an echoendoscope, an enteroscope, an esophagoscope, a gastroscope, a laryngoscope, a rhinolaryngoscope, a sigmoidoscope, and a duodenoscope.

The endoscope can have at least one interior conduit and the disinfectant is recirculated through the at least one interior conduit.

When the article 901 is positioned within a portion of the outflow 998, the process indicator of the article 901 can contact the disinfectant. A predetermined disinfectant exposure criterion can exist for contacting the disinfectant with the medical device 990. Generally, a predetermined disinfectant exposure criterion corresponds to an industry recognized standard for disinfection of the medical device 990. The predetermined disinfectant exposure criterion may correspond to an industry and/or governmental standard and/or guidelines or protocol for disinfection of the medical device, or the medical device manufacturer's specific disinfection procedure. Examples include ANSI/AAMI ST91:2015 "Flexible and semi-rigid endoscopic processing in health care facilities", American National Standards Institute, Washington, D.C., and "Standards of Infection Prevention in Reprocessing of Flexible Gastrointestinal Endoscopes", Society of Gastroenterology Nurses and Associates, Inc. (SGNA), Chicago, Ill., 2015.

The disinfection device 900 can be set up in parallel. For example, disinfectant is recirculated through medical device 990 and article 901 by a pump. Disinfectant can be diverted through tubing such that the article 901 is in parallel flow with the medical device 990.

After completion of a disinfecting cycle, the user may observe (e.g., visually or instrumentally) the article 901 to determine whether the predetermined disinfectant exposure (e.g., minimum effective concentration (MEC), time, and/or temperature) was achieved. If not, the process may be continued or restarted. Examples of instrumental methods for observing the process indicator include observation by human eye, reflectance spectroscopy, transmission spectroscopy, fluorescence spectroscopy, phosphorescence spectroscopy, and electrical capacitance. Such methods are well known in the art, and may use corresponding commercially available equipment.

If observation of the article 901 indicates inadequate disinfection relative to a predetermined disinfectant exposure criterion (i.e., FAIL), further processing would ordinarily be carried out until the article 901 indicates adequate disinfection relative to the predetermined disinfectant exposure criterion (i.e., PASS), or the medical device 990 can be optionally re-cleaned and the entire process repeated. If observation of the article 901 indicates adequate disinfection relative to the predetermined disinfectant exposure criterion (i.e., PASS), then the disinfection/cleaning process can be discontinued.

A user can spectrally observe (e.g., by reflectance, transmission, and/or fluorescence spectroscopy) the article 901 and obtaining at least one parameter (e.g., reflectance, transmission, and/or fluorescence at one or more wavelengths) therefrom that is predictive of the predetermined disinfectant exposure criterion. For example, observation may be made at one or more wavelengths, which may optionally be compared to a reference wavelength. The parameter to be monitored may be any parameter that correlates directly or indirectly with the amount of reaction product of the aldehyde(s) in the disinfectant with the process indicator that is formed. Exemplary parameters may include visible color (or color change), optical reflectance at one of more wavelengths, capacitance, and fluorescence at one or more wavelengths. The parameter(s) may be obtained continuously or periodically.

Additionally, it can be determined whether the predetermined disinfectant exposure criterion has been achieved. This step typically involves comparing the observed parameter to a value of the parameter corresponding to the predetermined disinfectant exposure criterion, and then determining that the predetermined disinfectant exposure criterion has been achieved. If not, the process is continued until the predetermined disinfectant exposure criterion is met, or the entire cycle is repeated.

Figure 10:
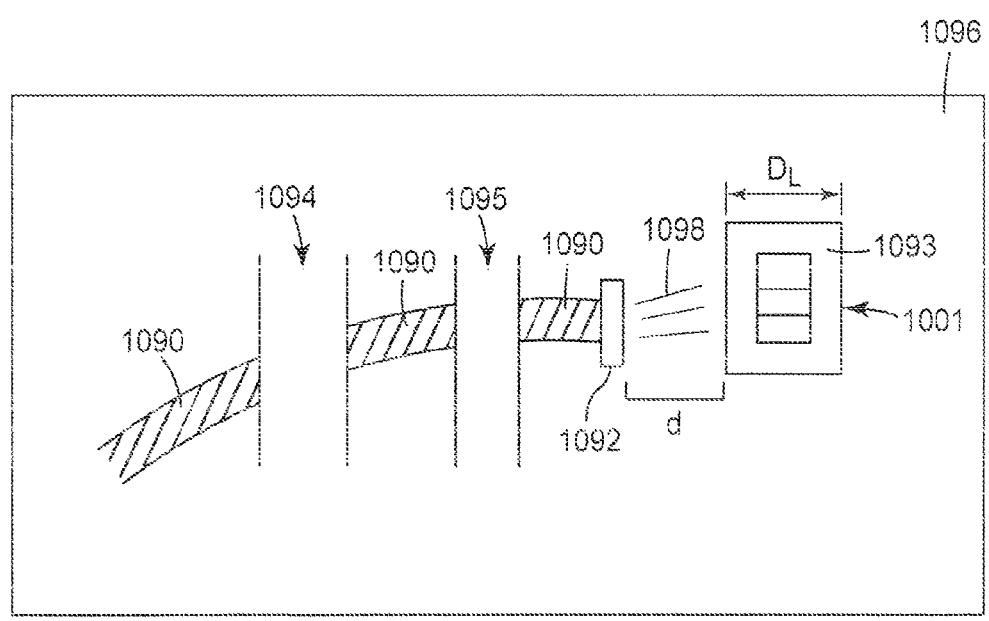
FIG. 10 is an elevational view of a mounting guide.

FIG. 10 illustrates a mounting guide 1096 that can be used with the article 1001. The mounting guide 1096 can position the article 1001 consistently relative to the medical device 1090. In some embodiments, the mounting guide can be an instrument protector which is designed to protect the medical device 1090 (e.g., an endoscope) from impacts. In other embodiments, the mounting guide 1096 may provide limited or no protection to the medical device 1090. The mounting guide 1096 can be made from a rigid material that is preferably antimicrobial and is structurally resistant to disinfectant conditions. Example materials include polymers, papers, or even ceramics. The mounting guide 1096 can have one or more securing means (e.g., 1094, 1095). The securing means (e.g., 1094, 1095) can secure the medical device 1090 to the mounting guide 1096 and can be rubber, polymers, or even metal clips.

As shown in FIG. 10, the securing means (e.g., 1094, 1095) are vertical slits formed from a body of the mounting guide 1096. The securing means 1095 can secure the tip of the medical device 1090. Securing means 1095 can be formed from a first vertical slit and a second vertical slit on the mounting guide 1095 allowing the medical device 1090 to be threaded through the slits. Likewise, securing means 1094 can further prevent movement of the medical device 1090 and can be formed similar to securing means 1095.

The mounting guide 1096 can also have one or more marked regions 1092, 1093 for the placement of a medical article 1001 as described above. The marked region 1092 can provide a visual indication of how to position the medical device 1090. The marked region 1093 can provide a visual indication of how to position the article 1001 described herein. The positioning defined by the marked region 1092 can maintain a particular standoff distance d for a disinfectant outflow 1098.

LIST OF ILLUSTRATIVE EMBODIMENTS

Embodiment 1

An article, comprising:
a first substrate having a first major surface and opposite ends; and
a process indicator disposed on at least a portion of the first major surface;
wherein a flow channel is formed by a portion of the process indicator and extends between the opposite ends.

Embodiment 1a

The article of any of the preceding embodiments, wherein a fluid transported through the flow channel contacts the process indicator.

Embodiment 1b

The article of any of the preceding embodiments, wherein a first wall of the flow channel is formed by a portion of the process indicator.

Embodiment 1c

The article of any of the preceding embodiments, further comprising a second substrate having a first major surface, wherein flow channel is further formed by a portion of the first major surface of the second substrate.

Embodiment 1d

The article of any of the preceding embodiments, wherein a second wall of the flow channel is formed by a portion of the first major surface of the second substrate.

Embodiment 1e

The article of any of the preceding embodiments, wherein the opposite ends comprise a first end and a second end, wherein flow channel defines a fluid pathway of a disinfectant from the first end through the second end.

Embodiment 1f

The article of any of the preceding embodiments, wherein the process indicator chemically reacts with at least one liquid disinfectant selected from the group consisting of glutaraldehyde, ortho-phthalaldehyde, hydrogen peroxide, and peroxyacetic acid.

Embodiment 2

The article of any of the preceding embodiments, wherein the process indicator is sandwiched between the first substrate and the second substrate.

Embodiment 3

The article of any of the preceding embodiments, wherein the first substrate has at least one face.

Embodiment 4

The article of any of the preceding embodiments, wherein the second substrate is coupled to at least a portion of the process indicator.

Embodiment 5

The article of any of the preceding embodiments, wherein the second substrate is secured to at least a portion of the first substrate.

Embodiment 6

The article of any of the preceding embodiments, wherein the first substrate has at least a first longitudinal face.

Embodiment 7

The article of any of the preceding embodiments, wherein the first longitudinal face is parallel to the flow channel.

Embodiment 8

The article of any of the preceding embodiments, wherein the first longitudinal face is defined by the length of the first substrate along a longitudinal axis.

Embodiment 9

The article of any of the preceding embodiments, wherein the second substrate is secured to at least a portion of the first substrate through at least a region defined by the first longitudinal face of the first substrate.

Embodiment 9a

The article of any of the preceding embodiments, wherein the region is further defined by a distance of no greater than 30% of the width of the first substrate.

Embodiment 9b

The article of any of the preceding embodiments, wherein the flow channel is defined by the region.

Embodiment 10

The article of any of the preceding embodiments, wherein the first substrate has at least a first lateral face.

Embodiment 11

The article of any of the preceding embodiments, wherein second substrate is not secured to the first substrate through the first lateral face.

Embodiment 12

The article of any of the preceding embodiments, wherein the process indicator is disposed on the entire surface of the first substrate.

Embodiment 13

The article of any of the preceding embodiments, wherein the first substrate is laminated paper.

Embodiment 14

The article of any of the preceding embodiments, wherein the first substrate is a polymer.

Embodiment 15

The article of any of the preceding embodiments, wherein the first substrate is a polyethylene terephthalate (PET) film.

Embodiment 16

The article of any of the preceding embodiments, wherein the PET film has a thickness of no greater than 10 thousandths of an inch.

Embodiment 17

The article of any of the preceding embodiments, wherein the first substrate has at least a first longitudinal face and a second longitudinal face.

Embodiment 18

The article of any of the preceding embodiments, wherein the second substrate is secured to at least a portion of the first substrate through at least the second longitudinal face of the first substrate.

Embodiment 19

The article of any of the preceding embodiments, wherein the first major surface of the second substrate is hydrophobic.

Embodiment 20

The article of any of the preceding embodiments, wherein the first major surface of the second substrate is hydrophilic.

Embodiment 21

The article of any of the preceding embodiments, wherein the first major surface of the first substrate is hydrophobic.

Embodiment 22

The article of any of the preceding embodiments, wherein the first major surface of the first substrate is hydrophilic.

Embodiment 23

The article of any of the preceding embodiments, further comprising a spacing element.

Embodiment 23a

The article of any of the preceding embodiments, wherein the spacing element is sandwiched between the process indicator and the second substrate.

Embodiment 23b

The article of any of the preceding embodiments, wherein the spacing element is disposed in at least a portion of the flow channel.

Embodiment 24

The article of any of the preceding embodiments, wherein the spacing element is a non-woven article.

Embodiment 24a

The article of any of the preceding embodiments, wherein the spacing element is a sponge.

Embodiment 25

The article of any of the preceding embodiments, wherein the spacing element is a tube.

Embodiment 26

The article of any of the preceding embodiments, wherein the tube has a plurality of openings formed from a body of the tube.

Embodiment 27

The article of any of the preceding embodiments, wherein the spacing element is integrated with the second substrate.

Embodiment 28

The article of any of the preceding embodiments, wherein the spacing element comprises a first member that extends at least a portion the length of the second substrate and is non planar to the second substrate.

Embodiment 29

The article of any of the preceding embodiments, wherein the first member is positioned to form an angle relative to the second substrate of about 90 degrees.

Embodiment 30

The article of any of the preceding embodiments, wherein the first member comprises a portion that extends away from the first member and is parallel to the second substrate.

Embodiment 31

The article of any of the preceding embodiments, wherein the first member extends the entire length of the second substrate.

Embodiment 32

The article of any of the preceding embodiments, wherein the spacing element comprises a second member that extends at least a portion the length of the second substrate and is non planar to the second substrate.

Embodiment 33

The article of any of the preceding embodiments, wherein the spacing element comprises a plurality of members.

Embodiment 34

The article of any of the preceding embodiments, wherein the second substrate is a microreplicated surface.

Embodiment 35

The article of any of the preceding embodiments, wherein the height of the first member is at least 0.01 millimeters.

Embodiment 36

The article of any of the preceding embodiments, wherein the plurality of members comprises a second member, wherein the first member is spaced apart at least 0.05 millimeters from the second member.

Embodiment 37

The article of any of the preceding embodiments, wherein an face of the first member is straight and positioned to form an angle of no greater 45 degrees with an face of the second substrate.

Embodiment 38

The article of any of the preceding embodiments, wherein the opposite ends have a distance of no greater than 4 inches.

Embodiment 39

The article of any of the preceding embodiments, wherein the opposite ends have a distance of no greater than 3 inches.

Embodiment 40

The article of any of the preceding embodiments, wherein the opposite ends have a distance of no greater than 2 inches.

Embodiment 41

The article of any of the preceding embodiments, wherein the opposite ends have a distance of no greater than 0.5 inches.

Embodiment 42

The article of any of the preceding embodiments, wherein the opposite ends have a distance of no greater than 0.375 inches.

Embodiment 43

The article of any of the preceding embodiments, wherein the opposite ends have a distance of no greater than 0.25 inches.

Embodiment 44

The article of any of the preceding embodiments, wherein the opposite ends have a distance of no greater than 0.125 inches.

Embodiment 44a

The article of any of the preceding embodiments, wherein a ratio of length to width of the first substrate is no greater than 5:1.

Embodiment 44b

The article of any of the preceding embodiments, wherein a ratio of length to width of the first substrate is no greater than 4:1.

Embodiment 44c

The article of any of the preceding embodiments, wherein a ratio of length to width of the first substrate is no greater than 3:1.

Embodiment 44d

The article of any of the preceding embodiments, wherein a ratio of length to width of the first substrate is no greater than 2:1.

Embodiment 45

The article of any of the preceding embodiments, further comprising a funneling device positioned adjacent the flow channel.

Embodiment 46

The article of any of the preceding embodiments, wherein the funneling further is positioned to direct disinfectant into the flow channel.

Embodiment 47

The article of any of the preceding embodiments, wherein the composition further comprises an aqueous liquid vehicle in which the compound is dispersed or dissolved.

Embodiment 48a

The article of any of the preceding embodiments, wherein the process indicator is selected from the group consisting of sodium sulfite, ammonium chloride, ammonium bromide, ammonium bicarbonate, ammonium acetate, and combinations thereof.

Embodiment 48b

The article of any of the preceding embodiments, wherein the process indicator comprises a synthetic amine-containing compound disposed on at least a portion of the first major surface, wherein the synthetic amine-containing compound comprises at least one of primary amino groups or secondary amino groups.

Embodiment 48c

The article of any of the preceding embodiments, wherein the synthetic amine-containing compound comprises a synthetic amine-containing polymer.

Embodiment 48d

The article of any of the preceding embodiments, wherein the synthetic amine-containing polymer comprises at least one of:
i) branched polyethylenimine;
ii) branched polyethylenimine that has been e-beam grafted to the substrate;
iii) crosslinked branched polyethylenimine;
iv) crosslinked branched guanylated polyethylenimine; or
v) crosslinked branched silylated polyethylenimine.

Embodiment 49

The article of any of the preceding embodiments, wherein the crosslinked branched silylated polyethylenimine comprises a crosslinked reaction product of a polyethylenimine with a compound containing at least two amine-reactive groups.

Embodiment 49a

The article of any of the preceding embodiments, wherein the compound is least one an amine-reactive organosilane coupling agent represented by the formula:

$$R^3-Z-SiY_3$$

wherein:
$R^3$ represents an amine-reactive group containing 1 to 12 carbon atoms;
Z represents a divalent organic group containing 1 to 8 carbon atoms; and
each Y independently represents a hydrolyzable group.

Embodiment 49b

The article of any of the preceding embodiments further comprising an aqueous liquid vehicle in which the compound is dispersed or dissolved.

Embodiment 49c

The article of any of the preceding embodiments, wherein $R^3$ has from 1 to 3 carbon atoms.

Embodiment 49d

The article of any of the preceding embodiments, wherein $R^3$ is selected from the group consisting of an isocyanato group, an oxiranyl group, a glycidoxy group, an acryloxy group, a carboethoxy group, a carbomethoxy group, a vinylsulfonyl group, and an acrylamido group.

Embodiment 49e

The article of any of the preceding embodiments, wherein Z further contains from 1 to 6 heteroatoms selected from the group consisting of O, N, and S.

Embodiment 49f

The article of any of the preceding embodiments, wherein Z comprises an alkylene group containing 1 to 3 carbon atoms.

Embodiment 49g

The article of any of the preceding embodiments, wherein each Y is independently selected from methoxy, ethoxy, hydroxy, acetoxy, chlorine, and bromine.

Embodiment 49h

The article of any of the preceding embodiments, wherein the at least one an amine-reactive hydrolyzable organosilane is selected from the group consisting of 3-isocyanatopropyltriethoxysilane, 3-isocyanatopropyltrimethoxysilane, 2-isocyanatoethyltriethoxysilane, 2-isocyanatoethyltrimethoxy, 3-acryloxypropyltriethoxysilane, 3-acryloxypropyltrimethoxysilane, 2-acryloxyethyltriethoxysilane, 2-acryloxyethyltrimethoxysilane, 2,3-epoxypropyltrimethoxysilane, 2,3-epoxypropyltriethoxysilane, 3-glycidoxypropyltriethoxysilane, and 3-glycidoxypropyltrimethoxysilane.

Embodiment 49i

The article of any of the preceding embodiments, further comprising a polymeric binder material.

Embodiment 50

The article of any of the preceding embodiments, wherein the synthetic amine-containing polymer comprises an amine-functional polysiloxane.

Embodiment 51

The article of any of the preceding embodiments, wherein the synthetic amine-containing compound comprises a polyethylenimine that is chemically bonded to silica.

Embodiment 52

The article of any of the preceding embodiments, wherein the first substrate comprises a second major surface.

Embodiment 53

The article of any of the preceding embodiments, further comprising a polymer film disposed on the second major surface of the first surface.

Embodiment 54

The article of any of the preceding embodiments, wherein the polymer film is a PET film.

Embodiment 55

The article of any of the preceding embodiments, wherein the PET film has a thickness of no greater than 10 thousandths of an inch.

Embodiment 56

The article of any of the preceding embodiments, further comprising an adhesive disposed between the second major surface of the first surface and the polymer film.

Embodiment 57

The article of any of the preceding embodiments, wherein the second substrate comprises a second major surface, further comprising an adhesive disposed on the second major surface of the second surface.

Embodiment 58

The article of any of the preceding embodiments, wherein the adhesive is a pressure sensitive adhesive.

Embodiment 59

A kit comprising:
the article of any of the preceding embodiments.

Embodiment 60

The kit of any of the preceding embodiments, further comprising:
a release liner;
a cutting device.

Embodiment 61

The kit of any of the preceding embodiments, further comprising:
a mounting guide.

Embodiment 61a

The kit of any of the preceding embodiments, wherein the mounting guide has one or more slits for positioning a medical device.

Embodiment 62

The kit of any of the preceding embodiments, wherein the mounting guide is configured to position the medical device such that an outflow of disinfectant from a medical device has a standoff distance of no greater than 2 inches.

Embodiment 63

The kit of any of the preceding embodiments, wherein the standoff distance is marked on the mounting guide.

Embodiment 63

A method comprising:
positioning a medical device within a sterilizing device, wherein, when a disinfectant flows through the sterilizing device, an outflow is produced;
positioning the article of any of the preceding embodiments within a portion of the outflow; and
contacting the disinfectant with the process indicator, wherein a predetermined disinfectant exposure criterion exists for contacting the disinfectant with the medical device.

Embodiment 64

The method of any of the preceding embodiments, further comprising:
spectrally observing the process indicator and obtaining at least one parameter therefrom that is predictive of the predetermined disinfectant exposure criterion; and
determining that the predetermined disinfectant exposure criterion has been achieved.

Embodiment 65

The method of any of the preceding embodiments, wherein the disinfectant comprises at least one dialdehyde.

Embodiment 66

The method of any of the preceding embodiments, wherein the disinfectant comprises at least one of flutaraldehyde or ortho-phthalaldehyde.

Embodiment 67

The method of any of the preceding embodiments, wherein the predetermined disinfectant exposure criterion corresponds to an industry recognized standard for disinfection of the medical device.

Embodiment 68

The method of any of the preceding embodiments, wherein the medical device comprises an endoscope having at least one interior conduit, and wherein the disinfectant is recirculated through the at least one interior conduit.

Embodiment 69

The method of any of the preceding embodiments, wherein the at least one parameter comprises optical reflectance.

Embodiment 70

The method of any of the preceding embodiments, wherein the at least one parameter comprises a visible color.

Embodiment 71

The method of any of the preceding embodiments, wherein the at least one process parameter indicator is continuously obtained.

Embodiment 72

The method of any of the preceding embodiments, wherein positioning the article comprises:
positioning the article such that at least a portion of the flow channel is oriented toward the outflow.

Embodiment 73

The method of any of the preceding embodiments, wherein positioning the article comprises:
positioning the article such that a majority of the flow channel is oriented toward the outflow.

Embodiment 74

The method of any of the preceding embodiments, wherein positioning the article comprises:

positioning the article such that the standoff distance between the outflow of the medical device and the flow channel is no greater than 3 inches.

Embodiment 75

The method of any of the preceding embodiments, wherein the standoff distance between the outflow of the medical device and the flow channel is no greater than 2 inches.

Embodiment 76

The method of any of the preceding embodiments, wherein the standoff distance between the outflow of the medical device and the flow channel is no greater than 1 inch.

Embodiment 77

The method of any of the preceding embodiments, further comprising contacting the medical device with a mounting guide, wherein the positioning the article comprises positioning the article on the mounting guide.

Examples

Sample Preparation (EX1-EX2):

Example 1 (EX1)

A substrate material was prepared by laminating an about 2.5 mil thick polyester/ionomer film (commercially available under the trade designation SURLYN from E. I. du Pont de Nemours and Company (Wilmington, Del.)) onto one side of Whatman 410 Grade filter paper (about 7.3 mil thick). A branched polyethylenimine (MW 60,000 g/mole as a 50 wt. % solution in water, available from Thermo Fisher Scientific, Waltham, Mass.) was diluted to 10 wt. % with added distilled water. This solution was coated onto the paper side of the substrate material as described in Example PI4 of U.S. Application Nos. 62/332,243, filed May 5, 2016 using reverse gravure printing. The coated substrate was then dried at 100° C. for 5 minutes to form a polyethyleneamine chemical indicator (PEI CI) and cut to a 1 cm×5 cm size unit.

The PEI CI was adhered to the adhesive side of an adhesive-coated 10-mil polyester terephthalate (PET) top film (the adhesive was 2 mil thick and commercially available from the 3M Company as 300 LSE Transfer Adhesive), with the PET film side of the PEI CI facing the adhesive and the PEI-coated Whatman paper side facing away from the adhesive. The PET film was commercially available from the 3M Company under the model number Series 990 Polyester Film 9901000, which has a hydrophilic treated side and an opposite non treated hydrophobic side. The PEI CI was then sandwiched between a bottom layer of 3M Condensation Management Film (available from 3M Company of St. Paul, Minn.) which is a microreplicated moisture management tape, and the adhesive-coated 10-mil PET top film, such that the PEI coated side was facing the microreplicated surface of the Condensation Management Film. In this construction, a series of channels is formed lengthwise between the PEI CI strip and the microreplicated surface.

Example 2 (EX2)

Example 1 (EX1) was repeated with the following exceptions. A branched polyethylenimine (abbreviation of bPEI, MW 60,000 g/mole as a 50 wt. % solution in water) was mixed with a 30 wt. % polyurethane dispersion (available as model #CS 8057, Incorez Copolymer Ltd., United Kingdom) and distilled water to form a coating formulation with a ratio of 1:1 by weight bPEI:polyurethane dispersion. This polyurethane/polyethylenimine (PU/PEI) composition was coated directly onto the 10-mil PET film instead of the paper side of the laminated paper.

Test Method:

An endoscope (model Olympus PCF Type S, from Olympus Corporation (Japan)), was placed into the basin of an AER (commercially available as model DSD-201 from Medivators Inc. (Minneapolis, Minn.). A standard AER cycle with no detergent wash phase was run using 0.35% OPA as the disinfectant. The flow rate of the disinfectant out of the endoscope was approximately 800 ml/min. The exemplary articles were placed in the direct flow path of the endoscope for one cycle. The color definition was recorded in Table 1.

TABLE 1

| Example | Binder/Indicator | First Substrate | Second Substrate | Color Definition |
| --- | --- | --- | --- | --- |
| EX1 | none/PEI | Paper side of Laminated Paper | Microreplicated Surface | Excellent Color development |
| EX2 | Polyurethane/PEI | 10-mil PET film | Microreplicated Surface | Good color development |

Sample Preparation (EX3-EX5):

Example 3 (EX3)

Example 1 (EX1) was repeated with the following exceptions. A process indicator of PU/PEI composition was sandwiched between a top and bottom layer of 10-mil PET film, such that the PU/PEI coated side of the PU/PEI CI was facing the hydrophilic treated side of the bottom of the PET film (3M Series 990 Polyester Film 9901000). In this construction, a single channel with a width of the PU/PEI CI is formed lengthwise between the PU/PEI CI strip and the hydrophilic treated surface of the PET bottom film. The PET bottom film was adhered to the entire length of the article (along the edges) using 3M 300 LSE transfer adhesive, with no adhesive directly between the PU/PEI CI and the bottom PET film. The channel was formed between the PET bottom film and the PEI CI. The adhesive used to adhere the label samples to the AER basin walls was available from the 3M Company as a VHB transfer adhesive.

Example 4 (EX4)

A sample was prepared the same as EX3 except that the PU/PEI CI faced the non-treated hydrophobic side of the bottom PET film. In this construction, a single channel the width of the PU/PEI CI is formed lengthwise between the PEI CI strip and the non-treated hydrophobic surface of the PET bottom film.

Example 5 (EX5)

A sample was prepared the same as CE1 except that a PEI indicator was used in place of the PU/PEI indicator.

Test Method:

An endoscope (model Olympus PCF Type S, from Olympus Corporation (Japan)), was placed into the basin of an AER (commercially available as model DSD-201 from Medivators Inc. (Minneapolis, Minn.). A standard AER cycle with no detergent wash phase was run using 0.35% OPA as the disinfectant. The flow rate of the disinfectant out of the endoscope was approximately 800 ml/min. The exemplary articles were placed in the direct flow path of the endoscope for one cycle. The color definition was recorded and ranked in table 2 (with 1 having the most color definition).

TABLE 2

| Example | Binder/Indicator | First Substrate | Second Substrate | Color Definition Rank |
|---|---|---|---|---|
| EX3 | PU/PEI | Laminated Paper | 10-mil PET film (hydrophilic surface) | 1 |
| EX4 | PU/PEI | Laminated Paper | 10-mil PET film (hydrophobic surface) | 2 |
| EX5 | PEI | Laminated Paper | 10-mil PET film (hydrophobic) | 3 |

Sample Preparation (EX6-EX10):

Example 6 (EX6)

Same as EX4 above, with the following exceptions. Turning to FIG. 6, the width of the chemical indicator strip x was held constant at 0.5 inches. The distance s and t were 1 inch. The distance v and u were zero. The length 1 of the strip was 2 inches.

Example 7 (EX7)

A sample was prepared the same as in EX6 except that length 1 was 2.5 inches.

Example 8 (EX8)

A sample was prepared the same as in EX6 except that length 1 was 3 inches.

Example 9 (EX9)

A sample was prepared the same as in EX6 except that length 1 was 3.5 inches.

Example 10 (EX10)

A sample was prepared the same as in EX6 except that length 1 was 4 inches.

Test Method:

An endoscope (model Olympus PCF Type S, from Olympus Corporation (Japan)), was placed into the basin of an AER (commercially available as model DSD-201 from Medivators Inc. (Minneapolis, Minn.). A standard AER cycle was run using 0.35% OPA as the disinfectant. The flow rate of the disinfectant out of the endoscope was approximately 800 ml/min. The exemplary articles were placed in the direct flow path of the endoscope for one cycle, where the stand-off distance was 1 inch from the flow channel of the article to the tip of the endoscope. The cycle did not include a 15 minute detergent wash phase. The color definition was recorded and ranked in table 3.

TABLE 3

| Example | Flow Channel Length | Ratio of flow channel length to width | Second Substrate | Color Definition Rank |
|---|---|---|---|---|
| EX46 | 2 | 4:1 | 10-mil PET film (hydrophobic) | 1 |
| EX7 | 2.5 | 5:1 | 10-mil PET film (hydrophobic) | 2 |
| EX8 | 3 | 6:1 | 10-mil PET film (hydrophobic) | 3 |
| EX9 | 3.5 | 7:1 | 10-mil PET film (hydrophobic) | 4 |
| EX10 | 4 | 8:1 | 10-mil PET film (hydrophobic) | 5 |

Sample Preparation (EX11-EX14):

Example 11 (EX11)

Same as EX4 above, with the following exceptions. Turning to FIG. 6, length 1 of the chemical indicator strip x was held constant at 2 inches. The distance s and t were equal but varied with respect to the total width. The distance v and u were zero. The width x of the strip was 0.5 inches.

Example 12 (EX12)

A sample was prepared the same as in EX11 except that width x was 0.375 inches.

Example 13 (EX13)

A sample was prepared the same as in EX11 except that width x was 0.25 inches.

Example 14 (EX14)

A sample was prepared the same as in EX11 except that width x was 0.125 inches.

Test Method:

An endoscope (model Olympus PCF Type S, from Olympus Corporation (Japan)), was placed into the basin of an AER (commercially available as model DSD-201 from Medivators Inc. (Minneapolis, Minn.). A standard AER cycle was nm using 0.35% OPA as the disinfectant. The flow rate of the disinfectant out of the endoscope was approximately 800 ml/min. Turning to FIG. 9, the exemplary articles were placed in the direct flow path of the endoscope for one cycle, where the stand-off distance d was 1 inch from the flow channel of the article to the tip of the endoscope. The cycle did not include a 15 minute detergent wash phase. The color definition was recorded and ranked in table 4.

TABLE 4

| Example | Flow Channel width x | Ratio of flow channel length 1 to width x | Second Substrate | Color Definition |
|---|---|---|---|---|
| EX11 | 0.5 | 4:1 | 10-mil PET film (hydrophobic) | Superior |
| EX12 | 0.375 | 5.33:1 | 10-mil PET film (hydrophobic) | Minimum Color Change |
| EX13 | 0.25 | 8:1 | 10-mil PET film (hydrophobic) | Minimum Color Change |
| EX14 | 0.125 | 16:1 | 10-mil PET film (hydrophobic) | Minimum Color Change |

Sample Preparation (EX15-EX18):

Example 15 (EX15)

An indicating strip was prepared the same as in EX11. The stand-off distance was 1 inch.

Example 16 (EX16)

An indicating strip was prepared the same as in EX11. The stand-off distance was 1.5 inches.

Example 17 (EX17)

An indicating strip was prepared the same as in EX11. The stand-off distance was 2 inches.

Example 18 (EX18)

An indicating strip was prepared the same as in EX1. The stand-off distance was 3 inches.

Test Method:

An endoscope (model Olympus PCF Type S, from Olympus Corporation (Japan)), was placed into the basin of an AER (commercially available as model DSD-201 from Medivators Inc. (Minneapolis, Minn.). A standard AER cycle was run using 0.35% OPA as the disinfectant. The flow rate of the disinfectant out of the endoscope was approximately 800 ml/min. Turning to FIG. 9, the exemplary articles were placed in the direct flow path where the stand-off distance d varied from 1 inch to 3 inches from the flow channel of the article to the tip of the endoscope for one cycle. The cycle did not include a 15 minute detergent wash phase. The color definition was recorded in table 5.

TABLE 5

| Example | Stand-off distance | Color Definition and rank |
|---------|--------------------|---------------------------|
| EX6     | 1                  | Acceptable - 1            |
| EX7     | 1.5                | Acceptable - 2            |
| EX8     | 2                  | Acceptable - 3            |
| CE10    | 3                  | Minimum Color Change - 4  |

What is claimed is:

1. A method comprising
positioning a medical device within a sterilizing device, wherein, when a disinfectant flows through the sterilizing device, an outflow of the disinfectant is produced;
positioning an article within a portion of the outflow;
the article, comprising:
   a first substrate having a first major surface and opposite ends, wherein the opposite ends comprise a first end and a second end; and
   a process indicator disposed on at least a portion of the first major surface as a coating or film, wherein the process indicator is configured to react with at least one liquid disinfectant selected from the group consisting of glutaraldehyde, ortho-phthalaldehyde, hydrogen peroxide, peroxyacetic acid, and combinations thereof;
   wherein a flow channel is formed by a portion of the process indicator and extends between the opposite ends,
   wherein the flow channel defines a fluid pathway of a disinfectant from the first end through the second end; and
contacting a portion of the outflow with the process indicator of the article;
wherein positioning the article further comprises positioning the article such that a standoff distance between the outflow of the medical device and the flow channel is no greater than 3 inches.

2. The method of claim 1, wherein a first wall of the flow channel is formed by a portion of the process indicator.

3. The method of claim 1, further comprising a second substrate having a first major surface, wherein the flow channel is further formed by a portion of the first major surface of the second substrate.

4. The method of claim 3, wherein a second wall of the flow channel is formed by a portion of the first major surface of the second substrate.

5. The method of claim 3, wherein the process indicator is sandwiched between the first substrate and the second substrate.

6. The method of claim 3, further comprising a spacing element, wherein the spacing element is sandwiched between the process indicator and the second substrate.

7. The method of claim 6, wherein the spacing element comprises a plurality of members including a first member that extends at least a portion of the length of the second substrate and is non-planar to the second substrate, wherein the height of the first member is at least 0.01 millimeters.

8. The method of claim 1, wherein the first substrate is a polyethylene terephthalate (PET) film.

9. The method of claim 8, wherein the PET film has a thickness of no greater than 10 thousandths of an inch.

10. The method of claim 1, further comprising:
   wherein a predetermined disinfectant exposure criterion exists for contacting the disinfectant with the medical device, the method further comprising
   spectrally observing the process indicator and obtaining at least one parameter therefrom that is predictive of the predetermined disinfectant exposure criterion; and
determining that the predetermined disinfectant exposure criterion has been achieved.

11. The method of claim 1, wherein the first substrate is tube-shaped.

12. The method of claim 1, further comprising a funneling device positioned adjacent to the flow channel to direct disinfectant into the flow channel.

13. The method of claim 1, wherein the process indicator is selected from the group consisting of: sodium sulfite, ammonium chloride, ammonium bromide, ammonium bicarbonate, ammonium acetate, and combinations thereof.

* * * * *